US010195327B2

(12) United States Patent
Meyer et al.

(10) Patent No.: US 10,195,327 B2
(45) Date of Patent: *Feb. 5, 2019

(54) SENSING AND STORAGE SYSTEM FOR FLUID BALANCE

(71) Applicant: Medtronic, Inc., Minneapolis, MN (US)

(72) Inventors: Thomas E. Meyer, Stillwater, MN (US); William P. Hajko, Safety Harbor, FL (US); Thomas P. Hartranft, Clearwater, FL (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/701,641

(22) Filed: Sep. 12, 2017

(65) Prior Publication Data

US 2018/0001011 A1    Jan. 4, 2018

Related U.S. Application Data

(62) Division of application No. 14/566,674, filed on Dec. 10, 2014, now Pat. No. 10,098,993.

(51) Int. Cl.
*A61M 1/16* (2006.01)

(52) U.S. Cl.
CPC ........ *A61M 1/1601* (2014.02); *A61M 1/1647* (2014.02); *A61M 1/1696* (2013.01); *A61M 2205/3334* (2013.01); *A61M 2205/3365* (2013.01)

(58) Field of Classification Search
None
See application file for complete search history.

(56) References Cited

U.S. PATENT DOCUMENTS

| 3,091,098 A | 5/1963 | Bowers |
| 3,370,710 A | 2/1968 | Bluemle |
| 3,506,126 A | 4/1970 | Lindsay, Jr. |
| 3,608,729 A | 9/1971 | Haselden |

(Continued)

FOREIGN PATENT DOCUMENTS

| CN | 201510761050.6 | 8/2017 |
| DE | 3215003 | 4/1985 |

(Continued)

OTHER PUBLICATIONS

[NPL234] Lima, et. al., An electrochemical sensor based on nanostructure hollsndite-type manganese oxide for detection of potassium ion, Sensors, 2009, 6613-8625, 9.

(Continued)

*Primary Examiner* — Benjamin M Kurtz
(74) *Attorney, Agent, or Firm* — Kenneth Collier; Roger Hahn (57) ABSTRACT

A sensing and storage system for fluid balance during dialysis is provided. The sensing and storage system has flow sensors on either side of a dialyzer in a controlled volume dialysate flow path. The sensors are positioned so that no fluid can be added to or removed from the dialysate flow path between the sensors except for that which is added or removed by action of a control pump. The sensing and storage system can have a fluid removal line for the removal of fluid from the dialysate flow loop.

21 Claims, 2 Drawing Sheets

(56) References Cited

U.S. PATENT DOCUMENTS

| | | | |
|---|---|---|---|
| 3,669,878 | A | 6/1972 | Marantz |
| 3,669,880 | A | 6/1972 | Marantz |
| 3,692,648 | A | 9/1972 | Matloff |
| 3,776,819 | A | 12/1973 | Williams |
| 3,809,241 | A | 5/1974 | Alvine |
| 3,850,835 | A | 11/1974 | Marantz |
| 3,884,808 | A | 5/1975 | Scott |
| 3,902,490 | A | 9/1975 | Jacobsen |
| 3,939,069 | A | 2/1976 | Granger |
| 3,989,622 | A | 11/1976 | Marantz |
| 4,060,485 | A | 11/1977 | Eaton |
| 4,094,775 | A | 6/1978 | Mueller |
| 4,136,708 | A | 1/1979 | Cosentino |
| 4,142,845 | A | 3/1979 | Lepp |
| 4,201,555 | A | 5/1980 | Tkach |
| 4,209,392 | A | 6/1980 | Wallace |
| 4,269,708 | A | 5/1981 | Bonomini |
| 4,316,725 | A | 2/1982 | Hovind |
| 4,371,385 | A | 2/1983 | Johnson |
| 4,374,382 | A | 2/1983 | Markowitz |
| 4,376,707 | A | 3/1983 | Lehmann |
| 4,381,999 | A | 5/1983 | Boucher |
| 4,430,098 | A | 2/1984 | Bowman |
| 4,460,555 | A | 7/1984 | Thompson |
| 4,490,135 | A | 12/1984 | Troutner |
| 4,556,063 | A | 12/1985 | Thompson |
| 4,562,751 | A | 1/1986 | Nason |
| 4,581,141 | A | 4/1986 | Ash |
| 4,612,122 | A | 9/1986 | Ambrus |
| 4,650,587 | A | 3/1987 | Polak |
| 4,678,408 | A | 7/1987 | Mason |
| 4,685,903 | A | 8/1987 | Cable |
| 4,695,385 | A | 9/1987 | Boag |
| 4,715,398 | A | 12/1987 | Shouldice |
| 4,747,822 | A | 5/1988 | Peabody |
| 4,750,494 | A | 6/1988 | King |
| 4,816,162 | A | 3/1989 | Rosskopf et al. |
| 4,826,663 | A | 5/1989 | Alberti |
| 4,828,693 | A | 5/1989 | Lindsay |
| 4,885,001 | A | 12/1989 | Leppert |
| 4,900,308 | A | 2/1990 | Verkaart |
| 4,915,713 | A | 4/1990 | Buzza |
| 4,950,230 | A | 8/1990 | Kendell |
| 4,977,888 | A | 12/1990 | Rietter |
| 5,015,388 | A | 5/1991 | Pusineri |
| 5,032,265 | A | 7/1991 | Jha |
| 5,080,653 | A | 1/1992 | Voss |
| 5,092,886 | A | 3/1992 | Dobos-Hardy |
| 5,097,122 | A | 3/1992 | Coiman |
| 5,114,580 | A | 5/1992 | Ahmad |
| 5,127,404 | A | 7/1992 | Wyborny |
| 5,141,493 | A | 8/1992 | Jacobsen |
| 5,180,403 | A | 1/1993 | Kogure |
| 5,192,132 | A | 3/1993 | Pelensky |
| 5,230,702 | A | 7/1993 | Lindsay |
| 5,284,470 | A | 2/1994 | Beltz |
| 5,302,288 | A | 4/1994 | Meidl |
| 5,305,745 | A | 4/1994 | Zacouto |
| 5,308,315 | A | 5/1994 | Khuri |
| 5,318,750 | A | 6/1994 | Lascombes |
| 5,399,157 | A | 3/1995 | Goux |
| 5,419,347 | A | 5/1995 | Carruth |
| 5,441,049 | A | 8/1995 | Masano |
| 5,442,969 | A | 8/1995 | Troutner |
| 5,468,388 | A | 11/1995 | Goddard |
| 5,507,723 | A | 4/1996 | Keshaviah |
| 5,591,344 | A | 1/1997 | Kenley |
| 5,643,201 | A | 7/1997 | Peabody |
| 5,662,806 | A | 9/1997 | Keshaviah et al. |
| 5,683,432 | A | 11/1997 | Goedeke |
| 5,685,835 | A | 11/1997 | Brugger |
| 5,685,988 | A | 11/1997 | Malchesky |
| 5,702,536 | A | 12/1997 | Carruth |
| 5,744,031 | A | 4/1998 | Bene |
| 5,762,782 | A | 6/1998 | Kenley |
| 5,849,179 | A | 12/1998 | Emerson |
| 5,858,186 | A | 1/1999 | Glass |
| 5,863,421 | A | 1/1999 | Peter |
| 5,938,938 | A | 8/1999 | Bosetto |
| 5,944,684 | A | 8/1999 | Roberts |
| 5,948,251 | A | 9/1999 | Brugger |
| 6,048,732 | A | 4/2000 | Anslyn |
| 6,052,622 | A | 4/2000 | Holmstrom |
| 6,058,331 | A | 5/2000 | King |
| 6,114,176 | A | 9/2000 | Edgson et al. |
| 6,126,831 | A | 10/2000 | Goldau |
| 6,171,480 | B1 | 1/2001 | Lee |
| 6,230,059 | B1 | 5/2001 | Duffin |
| 6,248,093 | B1 | 6/2001 | Moberg |
| 6,251,167 | B1 | 6/2001 | Berson |
| 6,254,567 | B1 | 7/2001 | Treu |
| 6,264,680 | B1 | 7/2001 | Ash |
| 6,321,101 | B1 | 11/2001 | Holmstrom |
| 6,362,591 | B1 | 3/2002 | Moberg |
| 6,363,279 | B1 | 3/2002 | Ben-Haim |
| 6,521,184 | B1 | 2/2003 | Edgson et al. |
| 6,554,798 | B1 | 4/2003 | Mann |
| 6,555,986 | B2 | 4/2003 | Moberg |
| 6,589,229 | B1 | 7/2003 | Connelly |
| 6,593,747 | B2 | 7/2003 | Puskas |
| 6,602,399 | B1 | 8/2003 | Fromherz |
| 6,627,164 | B1 | 9/2003 | Wong |
| 6,666,840 | B1 | 12/2003 | Falkvall et al. |
| 6,676,608 | B1 | 1/2004 | Keren |
| 6,711,439 | B1 | 3/2004 | Bradley |
| 6,719,745 | B1 | 4/2004 | Taylor |
| 6,726,647 | B1 | 4/2004 | Sternby |
| 6,780,322 | B1 | 8/2004 | Bissler |
| 6,814,724 | B2 | 11/2004 | Taylor |
| 6,818,196 | B2 | 11/2004 | Wong |
| 6,824,524 | B1 | 11/2004 | Favre |
| 6,861,266 | B1 | 3/2005 | Sternby |
| 6,878,283 | B2 | 4/2005 | Thompson |
| 6,960,179 | B2 | 11/2005 | Gura |
| 7,023,359 | B2 | 4/2006 | Goetz |
| 7,033,498 | B2 | 4/2006 | Wong |
| 7,074,332 | B2 | 7/2006 | Summerton |
| 7,077,819 | B1 | 7/2006 | Goldau |
| 7,097,630 | B2 | 8/2006 | Gotch |
| 7,101,519 | B2 | 9/2006 | Wong |
| 7,153,693 | B2 | 12/2006 | Tajiri |
| 7,169,303 | B2 | 1/2007 | Sullivan |
| 7,208,092 | B2 | 4/2007 | Micheli |
| 7,241,272 | B2 | 7/2007 | Karoor |
| 7,276,042 | B2 | 10/2007 | Polaschegg |
| 7,279,031 | B1 | 10/2007 | Wright |
| 7,318,892 | B2 | 1/2008 | Connell |
| 7,326,576 | B2 | 2/2008 | Womble et al. |
| 7,435,342 | B2 | 10/2008 | Tsukamoto |
| 7,488,447 | B2 | 2/2009 | Sternby |
| 7,500,958 | B2 | 3/2009 | Asbrink |
| 7,537,688 | B2 | 5/2009 | Tarumi |
| 7,544,300 | B2 | 6/2009 | Brugger |
| 7,544,737 | B2 | 6/2009 | Poss |
| 7,563,240 | B2 | 7/2009 | Gross |
| 7,566,432 | B2 | 7/2009 | Wong |
| 7,575,564 | B2 | 8/2009 | Childers |
| 7,597,806 | B2 | 10/2009 | Uchi |
| 7,674,231 | B2 | 3/2010 | McCombie |
| 7,704,361 | B2 | 4/2010 | Garde |
| 7,736,507 | B2 | 6/2010 | Wong |
| 7,744,553 | B2 | 6/2010 | Kelly |
| 7,754,852 | B2 | 7/2010 | Burnett |
| 7,756,572 | B1 | 7/2010 | Fard |
| 7,776,210 | B2 | 8/2010 | Rosenbaum |
| 7,785,463 | B2 | 8/2010 | Bissler |
| 7,790,103 | B2 | 9/2010 | Shah |
| 7,794,141 | B2 | 9/2010 | Perry |
| 7,794,419 | B2 | 9/2010 | Paolini |
| 7,850,635 | B2 | 12/2010 | Polaschegg |
| 7,857,976 | B2 | 12/2010 | Bissler |
| 7,867,214 | B2 | 1/2011 | Childers |
| 7,896,831 | B2 | 3/2011 | Sternby |
| 7,922,686 | B2 | 4/2011 | Childers |

(56) References Cited

U.S. PATENT DOCUMENTS

| | | |
|---|---|---|
| 7,922,911 B2 | 4/2011 | Micheli |
| 7,947,179 B2 | 5/2011 | Rosenbaum |
| 7,955,290 B2 | 6/2011 | Karoor |
| 7,955,291 B2 | 6/2011 | Sternby |
| 7,967,022 B2 | 6/2011 | Grant |
| 7,981,082 B2 | 7/2011 | Wang |
| 7,988,854 B2 | 8/2011 | Tsukamoto |
| 8,002,726 B2 | 8/2011 | Karoor |
| 8,029,454 B2 | 10/2011 | Kelly |
| 8,034,161 B2 | 10/2011 | Gura |
| 8,066,658 B2 | 11/2011 | Karoor |
| 8,070,709 B2 | 12/2011 | Childers |
| 8,080,161 B2 | 12/2011 | Ding et al. |
| 8,087,303 B2 | 1/2012 | Beavis |
| 8,096,969 B2 | 1/2012 | Roberts |
| 8,180,574 B2 | 5/2012 | Lo |
| 8,183,046 B2 | 5/2012 | Lu |
| 8,187,250 B2 | 5/2012 | Roberts |
| 8,197,439 B2 | 6/2012 | Wang |
| 8,202,241 B2 | 6/2012 | Karakama |
| 8,246,826 B2 | 8/2012 | Wilt |
| 8,273,049 B2 | 9/2012 | Demers |
| 8,292,594 B2 | 10/2012 | Tracey |
| 8,303,532 B2 | 11/2012 | Hamada |
| 8,313,642 B2 | 11/2012 | Yu |
| 8,317,492 B2 | 11/2012 | Demers |
| 8,357,113 B2 | 1/2013 | Childers |
| 8,366,316 B2 | 2/2013 | Kamen |
| 8,366,655 B2 | 2/2013 | Kamen |
| 8,404,491 B2 | 3/2013 | Li |
| 8,409,441 B2 | 4/2013 | Wilt |
| 8,409,444 B2 | 4/2013 | Wong |
| 8,449,487 B2 | 5/2013 | Hovland |
| 8,491,517 B2 | 7/2013 | Karoor |
| 8,496,809 B2 | 7/2013 | Roger |
| 8,499,780 B2 | 8/2013 | Wilt |
| 8,500,672 B2 | 8/2013 | Caleffi |
| 8,500,676 B2 | 8/2013 | Jansson |
| 8,500,994 B2 | 8/2013 | Weaver |
| 8,512,271 B2 | 8/2013 | Moissl |
| 8,518,258 B2 | 8/2013 | Balschat |
| 8,518,260 B2 | 8/2013 | Raimann |
| 8,521,482 B2 | 8/2013 | Akonur |
| 8,535,525 B2 | 9/2013 | Heyes |
| 8,560,510 B2 | 10/2013 | Brueggerhoff |
| 8,562,822 B2 | 10/2013 | Roger |
| 8,580,112 B2 | 11/2013 | Updyke |
| 8,597,227 B2 | 12/2013 | Childers |
| 8,696,626 B2 | 4/2014 | Kirsch |
| 8,777,892 B2 | 7/2014 | Sandford |
| 8,903,492 B2 | 12/2014 | Soykan |
| 8,906,240 B2 | 12/2014 | Crnkovich |
| 9,144,640 B2 | 9/2015 | Pudil |
| 9,173,987 B2 | 11/2015 | Meyer |
| 2003/0010717 A1 | 1/2003 | Brugger |
| 2003/0080059 A1 | 5/2003 | Peterson |
| 2003/0097086 A1 | 5/2003 | Gura |
| 2003/0105424 A1 | 6/2003 | Karoor |
| 2003/0105435 A1 | 6/2003 | Taylor |
| 2003/0114787 A1 | 6/2003 | Gura |
| 2004/0019312 A1 | 1/2004 | Childers |
| 2004/0019320 A1 | 1/2004 | Childers |
| 2004/0068219 A1 | 4/2004 | Summerton |
| 2004/0082903 A1 | 4/2004 | Micheli |
| 2004/0099593 A1 | 5/2004 | DePaolis |
| 2004/0102732 A1 | 5/2004 | Naghavi |
| 2004/0143173 A1 | 7/2004 | Reghabi |
| 2004/0147900 A1 | 7/2004 | Polaschegg |
| 2004/0168969 A1 | 9/2004 | Sternby |
| 2004/0215090 A1 | 10/2004 | Erkkila |
| 2005/0006296 A1 | 1/2005 | Sullivan |
| 2005/0065760 A1 | 3/2005 | Murtfeldt |
| 2005/0101901 A1 | 5/2005 | Gura |
| 2005/0113796 A1 | 5/2005 | Taylor |
| 2005/0115898 A1* | 6/2005 | Sternby ............... A61M 1/16 210/636 |
| 2005/0126961 A1 | 6/2005 | Bissler |
| 2005/0131331 A1 | 6/2005 | Kelly |
| 2005/0131332 A1 | 6/2005 | Kelly |
| 2005/0153904 A1 | 6/2005 | Fager |
| 2005/0126998 A1 | 7/2005 | Childers |
| 2005/0148923 A1 | 7/2005 | Sternby |
| 2005/0150832 A1 | 7/2005 | Tsukamoto |
| 2005/0234381 A1 | 10/2005 | Niemetz |
| 2005/0274658 A1 | 12/2005 | Rosenbaum |
| 2006/0025661 A1 | 2/2006 | Sweeney |
| 2006/0217771 A1 | 2/2006 | Soykan |
| 2006/0054489 A1 | 3/2006 | Denes |
| 2006/0076295 A1 | 4/2006 | Leonard |
| 2006/0157335 A1 | 7/2006 | Levine |
| 2006/0157413 A1 | 7/2006 | Bene |
| 2006/0186044 A1 | 8/2006 | Nalesso |
| 2006/0195064 A1 | 8/2006 | Plahey |
| 2006/0226079 A1 | 10/2006 | Mori |
| 2006/0241709 A1 | 10/2006 | Soykan |
| 2006/0264894 A1 | 11/2006 | Moberg |
| 2007/0007208 A1 | 1/2007 | Brugger |
| 2007/0066928 A1 | 3/2007 | Lannoy |
| 2007/0072285 A1 | 3/2007 | Barringer |
| 2007/0138011 A1 | 6/2007 | Hofmann |
| 2007/0175827 A1 | 8/2007 | Wariar |
| 2007/0179431 A1 | 8/2007 | Roberts et al. |
| 2007/0213653 A1 | 9/2007 | Childers |
| 2007/0213665 A1 | 9/2007 | Curtin et al. |
| 2007/0215545 A1 | 9/2007 | Bissler |
| 2007/0243113 A1 | 10/2007 | DiLeo |
| 2007/0255250 A1 | 11/2007 | Moberg |
| 2008/0006570 A1 | 1/2008 | Gura |
| 2008/0015493 A1 | 1/2008 | Childers et al. |
| 2008/0021337 A1 | 1/2008 | Li |
| 2008/0051696 A1 | 2/2008 | Curtin |
| 2008/0053905 A9 | 3/2008 | Brugger |
| 2008/0067132 A1 | 3/2008 | Ross |
| 2008/0093276 A1 | 4/2008 | Roger |
| 2008/0154543 A1 | 6/2008 | Rajagopal |
| 2008/0215247 A1 | 9/2008 | Tonelli |
| 2008/0217245 A1 | 9/2008 | Rambod |
| 2008/0230473 A1 | 9/2008 | Herbst |
| 2008/0253427 A1 | 10/2008 | Kamen |
| 2009/0012450 A1 | 1/2009 | Shah |
| 2009/0020471 A1 | 1/2009 | Tsukamoto |
| 2009/0078636 A1 | 3/2009 | Uchi |
| 2009/0084199 A1 | 4/2009 | Wright |
| 2009/0084721 A1 | 4/2009 | Yardimci |
| 2009/0101549 A1 | 4/2009 | Kamen |
| 2009/0101552 A1 | 4/2009 | Fulkerson |
| 2009/0101577 A1 | 4/2009 | Fulkerson |
| 2009/0105629 A1 | 4/2009 | Grant |
| 2009/0107335 A1 | 4/2009 | Wilt |
| 2009/0124963 A1 | 5/2009 | Hogard |
| 2009/0127193 A1 | 5/2009 | Updyke |
| 2009/0131858 A1 | 5/2009 | Fissell |
| 2009/0159527 A1 | 6/2009 | Mickols |
| 2009/0171261 A1 | 7/2009 | Sternby |
| 2009/0173682 A1 | 7/2009 | Robinson |
| 2009/0182263 A1 | 7/2009 | Burbank |
| 2009/0187138 A1 | 7/2009 | Lundtveit |
| 2009/0216045 A1 | 8/2009 | Singh |
| 2009/0223539 A1 | 9/2009 | Gibbel |
| 2009/0275849 A1 | 11/2009 | Stewart |
| 2009/0275883 A1 | 11/2009 | Chapman |
| 2009/0281484 A1 | 11/2009 | Childers |
| 2009/0282980 A1 | 11/2009 | Gura |
| 2009/0314063 A1 | 12/2009 | Sternby |
| 2010/0004588 A1 | 1/2010 | Yeh |
| 2010/0007838 A1 | 1/2010 | Fujimoto |
| 2010/0010429 A1 | 1/2010 | Childers |
| 2010/0022936 A1 | 1/2010 | Gura |
| 2010/0030151 A1 | 2/2010 | Kirsch |
| 2010/0042035 A1 | 2/2010 | Moissl |
| 2010/0051552 A1 | 3/2010 | Rohde |
| 2010/0078092 A1 | 4/2010 | Weilhoefer |
| 2010/0078381 A1 | 4/2010 | Merchant |

(56) References Cited

U.S. PATENT DOCUMENTS

| | | |
|---|---|---|
| 2010/0078387 A1 | 4/2010 | Wong |
| 2010/0084330 A1 | 4/2010 | Wong |
| 2010/0087771 A1 | 4/2010 | Karakama |
| 2010/0094158 A1 | 4/2010 | Solem |
| 2010/0100027 A1 | 4/2010 | Schilthuizen et al. |
| 2010/0102190 A1 | 4/2010 | Zhu et al. |
| 2010/0106071 A1 | 4/2010 | Wallenborg |
| 2010/0114012 A1 | 5/2010 | Sandford et al. |
| 2010/0130906 A1 | 5/2010 | Balschat |
| 2010/0137693 A1 | 6/2010 | Porras |
| 2010/0137782 A1 | 6/2010 | Jansson |
| 2010/0140149 A1 | 6/2010 | Fulkerson |
| 2010/0168546 A1 | 7/2010 | Kamath |
| 2010/0192686 A1 | 8/2010 | Kamen |
| 2010/0199670 A1 | 8/2010 | Robertson |
| 2010/0213127 A1 | 8/2010 | Castellarnau |
| 2010/0217180 A1 | 8/2010 | Akonur |
| 2010/0217181 A1 | 8/2010 | Roberts |
| 2010/0224492 A1 | 9/2010 | Ding |
| 2010/0234795 A1 | 9/2010 | Wallenas |
| 2010/0241045 A1 | 9/2010 | Kelly |
| 2010/0252490 A1 | 10/2010 | Fulkerson |
| 2010/0274171 A1 | 10/2010 | Caleffi |
| 2010/0282662 A1 | 11/2010 | Lee |
| 2010/0312172 A1 | 12/2010 | Hoffman |
| 2010/0312174 A1 | 12/2010 | Hoffman |
| 2010/0326911 A1 | 12/2010 | Rosenbaum |
| 2010/0327586 A1 | 12/2010 | Mardirossian |
| 2011/0009798 A1 | 1/2011 | Kelly |
| 2011/0017665 A1 | 1/2011 | Updyke |
| 2011/0048949 A1 | 3/2011 | Ding et al. |
| 2011/0066043 A1 | 3/2011 | Banet |
| 2011/0071465 A1 | 3/2011 | Wang |
| 2011/0077574 A1 | 3/2011 | Sigg |
| 2011/0079558 A1 | 4/2011 | Raimann |
| 2011/0087187 A1 | 4/2011 | Beck |
| 2011/0100909 A1 | 5/2011 | Stange |
| 2011/0105983 A1 | 5/2011 | Kelly |
| 2011/0106003 A1 | 5/2011 | Childers |
| 2011/0120930 A1 | 5/2011 | Mishkin |
| 2011/0120946 A1 | 5/2011 | Levin |
| 2011/0130666 A1 | 6/2011 | Dong |
| 2011/0132838 A1 | 6/2011 | Curtis |
| 2011/0144570 A1 | 6/2011 | Childers |
| 2011/0160637 A1 | 6/2011 | Beiriger |
| 2011/0163030 A1 | 7/2011 | Weaver |
| 2011/0163034 A1 | 7/2011 | Castellarnau |
| 2011/0184340 A1 | 7/2011 | Tan |
| 2011/0189048 A1 | 8/2011 | Curtis |
| 2011/0220562 A1 | 9/2011 | Beiriger |
| 2011/0247973 A1 | 10/2011 | Sargand |
| 2011/0272337 A1 | 11/2011 | Palmer |
| 2011/0284377 A1 | 11/2011 | Rohde |
| 2011/0297593 A1 | 12/2011 | Kelly |
| 2011/0315611 A1 | 12/2011 | Fulkerson |
| 2011/0315632 A1 | 12/2011 | Freije |
| 2013/0199998 A1* | 8/2013 | Kelly ............ A61M 1/1696 210/646 |
| 2013/0211730 A1 | 8/2013 | Wolff |
| 2013/0213890 A1 | 8/2013 | Kelly |
| 2013/0228516 A1 | 9/2013 | Jonsson |
| 2013/0228517 A1 | 9/2013 | Roger |
| 2013/0231607 A1 | 9/2013 | Roger |
| 2013/0248426 A1 | 9/2013 | Pouchoulin |
| 2013/0256227 A1 | 10/2013 | Kelly |
| 2013/0274642 A1 | 10/2013 | Soykan |
| 2013/0304020 A1 | 11/2013 | Wilt |
| 2013/0324915 A1 | 12/2013 | Britton |
| 2013/0330208 A1 | 12/2013 | Ly |
| 2013/0331774 A1 | 12/2013 | Farrell |
| 2014/0001112 A1 | 1/2014 | Karoor |
| 2014/0018727 A1 | 1/2014 | Burbank |
| 2014/0018728 A1 | 1/2014 | Plahey |
| 2014/0042092 A1 | 2/2014 | Akonur |
| 2014/0065950 A1 | 3/2014 | Mendelsohn |
| 2014/0088442 A1 | 3/2014 | Soykan |
| 2014/0110340 A1 | 4/2014 | White |
| 2014/0110341 A1 | 4/2014 | White |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0190885 A1 | 7/2014 | Meyer |
| 2014/0190886 A1 | 7/2014 | Pudil |
| 2014/0190891 A1 | 7/2014 | Lura |
| 2014/0216250 A1 | 8/2014 | Meyer |
| 2014/0217020 A1 | 8/2014 | Meyer |
| 2014/0217027 A1 | 8/2014 | Meyer |
| 2014/0217028 A1 | 8/2014 | Pudil |
| 2014/0217029 A1 | 8/2014 | Meyer |
| 2014/0217030 A1 | 8/2014 | Meyer |
| 2014/0220699 A1 | 8/2014 | Pudil |
| 2014/0224736 A1 | 8/2014 | Heide |
| 2014/0251908 A1 | 9/2014 | Ding |
| 2015/0057602 A1 | 2/2015 | Mason |
| 2015/0083647 A1 | 3/2015 | Meyer |
| 2015/0114891 A1 | 4/2015 | Meyer |
| 2015/0144539 A1 | 5/2015 | Pudil |
| 2015/0144542 A1 | 5/2015 | Pudil |
| 2015/0157960 A1 | 6/2015 | Pudil |
| 2015/0238673 A1 | 8/2015 | Gerber |
| 2015/0250937 A1 | 9/2015 | Pudil |
| 2015/0258268 A1 | 9/2015 | Collier |
| 2015/0352270 A1 | 12/2015 | Pudil |
| 2016/0038666 A1 | 2/2016 | Kelly |
| 2016/0166748 A1 | 6/2016 | Meyer |
| 2016/0166751 A1 | 6/2016 | Meyer |
| 2016/0166752 A1 | 6/2016 | Meyer |
| 2016/0166753 A1 | 6/2016 | Meyer |

FOREIGN PATENT DOCUMENTS

| | | |
|---|---|---|
| EP | 266795 A2 | 11/1987 |
| EP | 7111821 B1 | 6/2003 |
| EP | 2308526 | 10/2003 |
| EP | 2116269 | 2/2008 |
| EP | 2219703 | 5/2009 |
| EP | 2100553 A1 | 9/2009 |
| EP | 2398529 | 11/2010 |
| EP | 2575827 A2 | 12/2010 |
| EP | 2100553 | 8/2011 |
| EP | 2388030 | 11/2011 |
| EP | 2576453 A2 | 12/2011 |
| EP | 2701580 | 11/2012 |
| EP | 2701595 | 11/2012 |
| EP | 2344220 B1 | 4/2013 |
| EP | 2701596 | 3/2014 |
| EP | 2740502 | 6/2014 |
| FR | 2237639 | 2/1977 |
| JP | 2002306904 | 10/2002 |
| JP | 2006325668 A | 12/2006 |
| WO | 9532010 A1 | 11/1995 |
| WO | 9937342 | 7/1999 |
| WO | 9937342 A1 | 7/1999 |
| WO | WO2000057935 A1 | 10/2000 |
| WO | 2002043859 | 6/2002 |
| WO | 2003043677 A2 | 5/2003 |
| WO | 2003043680 | 5/2003 |
| WO | 2003051422 A2 | 6/2003 |
| WO | 2004008826 | 1/2004 |
| WO | 2004009156 | 1/2004 |
| WO | 2004030716 A2 | 4/2004 |
| WO | 2004030717 A2 | 4/2004 |
| WO | 2004064616 A2 | 8/2004 |
| WO | 2004062710 A3 | 10/2004 |
| WO | 2004105589 A2 | 12/2004 |
| WO | 2005044339 | 5/2005 |
| WO | 2004105589 A3 | 6/2005 |
| WO | 2005061026 | 7/2005 |
| WO | 2005123230 | 12/2005 |
| WO | 2005123230 A2 | 12/2005 |
| WO | 2006023589 | 3/2006 |
| WO | 2006124431 A2 | 11/2006 |
| WO | 2007010164 A2 | 1/2007 |

(56) References Cited

FOREIGN PATENT DOCUMENTS

| WO | 2007089855 A2 | 8/2007 |
|---|---|---|
| WO | 2007146162 A2 | 12/2007 |
| WO | 2007146162 A3 | 12/2007 |
| WO | 2008037410 | 4/2008 |
| WO | 2008051994 | 8/2008 |
| WO | 2009026603 | 12/2008 |
| WO | 2009024566 | 2/2009 |
| WO | 2009026603 A1 | 3/2009 |
| WO | 2009061608 | 5/2009 |
| WO | 2009064984 | 5/2009 |
| WO | 2009067071 A1 | 5/2009 |
| WO | 2009071103 | 6/2009 |
| WO | 2009094184 | 7/2009 |
| WO | 2009132839 A1 | 11/2009 |
| WO | 2009157877 A1 | 12/2009 |
| WO | 2009157878 A1 | 12/2009 |
| WO | 20090157877 | 12/2009 |
| WO | 2010028860 | 3/2010 |
| WO | 2010028860 A1 | 3/2010 |
| WO | 2010042666 | 4/2010 |
| WO | 2010042666 A2 | 4/2010 |
| WO | 2010052705 A1 | 5/2010 |
| WO | 2010062698 | 6/2010 |
| WO | 2010096659 | 10/2010 |
| WO | 2010121820 | 10/2010 |
| WO | 2010102190 A4 | 11/2010 |
| WO | 2011017215 A1 | 2/2011 |
| WO | 2011025705 A1 | 3/2011 |
| WO | 2010042666 A3 | 6/2012 |
| WO | 2013019994 A2 | 2/2013 |
| WO | 2013025844 | 2/2013 |
| WO | 2013025844 A2 | 2/2013 |
| WO | 2013027214 | 2/2013 |
| WO | 2013028809 A2 | 2/2013 |
| WO | 2013028809 A3 | 2/2013 |
| WO | 2013019994 A3 | 4/2013 |
| WO | 2013025844 A3 | 5/2013 |
| WO | 2013103607 A1 | 7/2013 |
| WO | 2013103906 | 7/2013 |
| WO | 2013110906 | 8/2013 |
| WO | 2013110919 | 8/2013 |
| WO | 2013114063 A1 | 8/2013 |
| WO | 2013121162 A1 | 8/2013 |
| WO | 2013140346 | 9/2013 |
| WO | 2013141896 | 9/2013 |
| WO | 2013188861 A1 | 12/2013 |
| WO | 2014117000 | 7/2014 |
| WO | 2014121158 A1 | 8/2014 |
| WO | 2014121162 | 8/2014 |
| WO | 2014121163 | 8/2014 |
| WO | 2014121167 | 8/2014 |
| WO | 2014121169 | 8/2014 |
| WO | 2015071247 A1 | 5/2015 |

OTHER PUBLICATIONS

[NPL235] Maclean, et, al., Effects of hindlimb contraction on pressor and muscle interstitial metabolite responses in the cat, J. App. Physiol., 1998, 1583-1592, 85(4).
[NPL237] U.S. Appl. No. 13/757,693, filed Feb. 1, 2013.
[NPL238] PCT Application, PCT/US20013/020404, filed Jan. 4, 2013.
[NPL23] U.S. Appl. No. 13/424,525.
[NPL240] U.S. Appl. No. 13/836,973, filed Mar. 15, 2013.
[NPL241] U.S. Appl. No. 14/259,655, filed Apr. 23, 2014.
[NPL242] U.S. Appl. No. 14/259,589, filed Apr. 23, 2014.
[NPL243] U.S. Appl. No. 13/757,693, filed Jan. 4, 2013.
[NPL244] U.S. Appl. No. 13/836,079, filed Mar. 15, 2013.
[NPL245] U.S. Appl. No. 14/240,129, filed Aug. 22, 2013.
[NPL246] PCT/US2014/014346 International Search Report and Written Opinion.
[NPL247] U.S. Appl. No. 13/835,735, filed Mar. 15, 2013.
[NPL248] PCT/US2014/014345 International Search Report and Written Opinion, dated May 2014.
[NPL250] U.S. Appl. No. 13/835,735 IDS, filed Jun. 13, 2013.
[NPL264] PCT/US2014/014357 International Search Report and Written Opinion.
[NPL264] PCT/US2014/014357 International Search Report and Written Opinion dated May 19, 2014.
[NPL268] Ronco et al. 2008, Cardiorenal Syndrome, Journal American College Cardiology, 52:1527-1539, Abstract.
[NPL26] Overgaard, et. al., Activity-induced recovery of excitability in K+-depressed rat soieus muscle, Am. J. P.
[NPL27] Overgaard. et. al., Relations between excitability and contractility in rate soleusmuscle: role of the Na+-K+ pump and Na+-K—S gradients. Journal of Physiology, 1999, 215-225, 518(1).
[NPL306] Coast, et al. 1990, An approach to Cardiac Arrhythmia analysis Using Hidden Markov Models, IEEE Transactions on Biomedical Engineering. 1990, 37(9):826-835.
[NPL309] Weiner, et. al., Article: Cardiac Function and Cardiovascular Disease in Chronic Kidney Disease, Book: Primer on Kidney Diseases (Author: Greenberg, et al), 2009,499-505, 5th Ed., Saunders Elsevier, Philadelphia, PA.
[NPL310] U.S. Appl. No. 61/480,532.
[NPL311] U.S. Appl. No. 13/424,479.
[NPL312] U.S. Appl. No. 13/424,429.
[NPL313] U.S. Appl. No. 13/424,525.
[NPL317] U.S. Appl. No. 61/480,530.
[NPL318] U.S. Appl. No. 61/480,528.
[NPL32] Secemsky, et. al, High prevalence of cardiac autonomic dysfunction and T-wave alternans in dialysis patients. Heart Rhythm, Apr. 2011, 592-598 : vol. 8, No. 4.
[NPL35] Wei, et. al., Fullerene-cryptand coated piezoelectric crystal urea sensor based on urease, Analytica Chimica Acta, 2001,77-85:437.
[NPL376] Gambro AK 96 Dialysis Machine Operators Manual, Dec. 2012.
[NPL377] European Search Report 12819714.2-1651/2739325 PCT/US2012049398, dated Jun. 12, 2015.
[NPL378] PCT/US2014/14343 Intl Search Report & Written Opinion, dated May 9, 2014.
[NPL379] PCT/US2014/014350 International Search Report and Written Opinion dated May 2014.
[NPL37] U.S. Appl. No. 13/368,225.
[NPL380] EP 14746793 Supplementary European Search Report dated Aug. 18, 2016.
[NPL381] EP 14746791 Supplementary European Search Report dated Aug. 19, 2016.
[NPL382] EP 14746799 Supplementary European Seach Report dated Aug. 18, 2016.
[NPL383] Leifer et al., A Study on the Temperature Variation of Rise Velocity for Large Clean Bubbles, J. Atmospheric & Oceanic Tech., vol. 17, pp. 1392-1402.
[NPL384] TALAIA, Terminal Velocity of a Bubble Rise in a Liquid Column, World Acad. of Sci., Engineering & Tech., vol. 28, pp. 264-268.
[NPL386] The FHN Trial Group. In-Center. Hemodialysis Six Times per Week versus Three Times per Week, New England Journal of Medicine, 2010 Abstract.
[NPL39] PCT/US2012/034332, International Search Report, dated Jul. 5, 2012.
[NPL462] Office Action in U.S. Appl. No. 13/757,717 dated Dec. 26, 2014.
[NPL463] Office Action in U.S. Appl. No. 13/757,709 dated Jun. 6, 2015.
[NPL464] Office Action in U.S. Appl. No. 13/757,709 dated Jan. 7, 2016.
[NPL465] Office Action in U.S. Appl. No. 13/757,728 dated Jan. 8, 2016.
[NPL466] Office Action in U.S. Appl. No. 13/757,728 dated Aug. 12, 2016.
[NPL467] Office Action in U.S. Appl. No. 13/757,796 dated Apr. 13, 2015.
[NPL468] Office Action in U.S. Appl. No. 13/757,796 dated Dec. 21, 2015.

(56) References Cited

OTHER PUBLICATIONS

[NPL469] Office Action in U.S. Appl. No. 13/836,538 dated Aug. 19, 2015.
[NPL46] Siegenthaler, et al., Pulmonary fluid status monitoring with intrathoracic impedance, Journal of Clinical Monitoring and Computing, 24:449-451, 2010.
[NPL470] Office Action in U.S. Appl. No. 13/836,538 dated Jan. 11, 2016.
[NPL471] Office Action in U.S. Appl. No. 13/836,538 dated Apr. 27, 2016.
[NPL472] Office Action in U.S. Appl. No. 13/757,722 dated May 19, 2016.
[NPL473] Office Action in U.S. Appl. No. 13/757,709 dated Jan. 7, 2016.
[NPL474] Office Action in U.S. Appl. No. 13/757,693 dated Nov. 13, 2015.
[NPL475] Office Action in U.S. Appl. No. 13/757,693 dated May 23, 2016.
[NPL476] Office Action in U.S. Appl. No. 13/757,709 dated Jun. 6, 2015.
[NPL47] U.S. Appl. No. 61/480,544.
[NPL481] Office Action in U.S. Appl. No. 13/757,794 dated Oct. 21, 2015.
[NPL482] Office Action in U.S. Appl. No. 13/757,794 dated May 2, 2016.
[NPL483] Office Action in U.S. Appl. No. 13/424,525 dated Aug. 11, 2015.
[NPL484] Office Action in U.S. Appl. No. 13/424,525 dated Feb. 25, 2016.
[NPL485] Office Action in U.S. Appl. No. 13/424,525 dated Jun. 17, 2016.
[NPL486] Office Action in U.S. Appl. No. 13/424,525 dated Oct. 20, 2016.
[NPL487] Office Action in U.S. Appl. No. 13/424,479 dated Nov. 24, 2014.
[NPL488] Office Action in U.S. Appl. No. 14/566,686 dated Apr. 28, 2016.
[NPL489] Office Action in U.S. Appl. No. 13/424,533 dated Oct. 22, 2013.
[NPL490] Office Action in U.S. Appl. No. 13/424,533 dated Apr. 18, 2014.
2017-530641_OA.
[NPL105] Brynda, et. al., The detection of toman 2-microglcbuiin by grating coupler immunosensor with three dimensional antibody networks. Biosensors & Bioelectronics, 1999, 363-368, 14(4).
[NPL10] Wheaton, et al., Dowex Ion Exchange Resins-Fundamentals of Ion Exchange; Jun. 2000, pp. 1-9. http://www.dow.com/scripts/litorder.asp?filepath=liquidseps/pdfs/noreg/177-01837.pdf.
[NPL111] Zhong, et. al., Miniature urea sensor based on H(+)-ion sensitive field effect transistor and its application in clinical analysis, Chin. J. Biotechnol., 1992, 57-65. 8(1).
[NPL119] PCT/US2012/034331, International Search Report and Written Opinion dated Jul. 9, 2012.
[NPL121] Roberts M, The regenerative dialysis (REDY) sorbent system. Nephrology, 1998, 275-278:4.
[NPL138] U.S. Appl. No. 61/480,544.
[NPL139] U.S. Appl. No. 61/480,541.
[NPL142] Hemametrics, Crit-Line Hematocrit Accuracy, 2003, 1-5, vol. 1, Tech Note No. 11 (Rev. D).
[NPL144] Weissman, S., et al., Hydroxyurea-induced hepatitis in human immunodeficiency virus-positive patients. Clin. Infec. Dis, (Jul. 29, 1999): 223-224.
[NPL146] PCT/US2012/034334, International Search Report, dated Jul. 6, 2012.
[NPL147] PCT/US2012/034335, International Search Report, dated Sep. 5, 2012.
[NPL148] PCT/US/2012/034327, International Search Report, dated Aug. 13, 2013.
[NPL149] PCT/US/2012/034329, International Search Report, dated Dec. 3, 2012.
[NPL161] EP13182115.9-1651 European Search Report, dated Feb. 3, 2014.
[NPL162] International Search Report from PCT/US2012/051946 dated Mar. 4, 2013.
[NPL163] U.S. Appl. No. 61/526,209.
[NPL164] Written Opinion of the International Searching Authority for PCT/US2012/049398 dated Feb. 25, 2013.
[NPL169] Wang, Fundamentals of intrathoracic impedance monitoring in heart failure, Am. J. Cardiology, 2007, 3G-10G: Suppl.
[NPL16] PCT/US2014/067650 International Search Report Written Opinion dated Mar. 9, 2015.
[NPL170] Bleyer, et al, Kidney International. Jun. 2006; 69(12):2268-2273.
[NPL172] U.S. Appl. No. 29/446,285, filed Feb. 1, 2013.
[NPL175] Marchant, et. al., In vivo Biocompatibility Studies 1: The Cage Implant System and a Biodegradable Hydrogel, J. Biomed. Mat. Res., 1983, 301-325: 17.
[NPL176] Bleyer, et. al., Sudden and cardiac death rated in hemodialysis patients, Kidney International. 1999, 1553-1559: 55.
[NPL178] PCT/US2012/025711, International Search Report dated Jul. 4, 2012.
[NPL179] PCT/US2013/020404, International Search Report, dated Jan. 4, 2013.
[NPL187] PCT/US2012/034333, International Preliminary Report on Patentability, dated Oct. 29, 2013.
[NPL188] PCT/US2012/034333, International Search Report, dated Aug. 29, 2012.
[NPL188] PCT/US2012/034333, International Search Report, dated Aug. 29, 2013.
[NPL189] PCT/US2012/051011, International Search Report, dated Jan. 17, 2014.
[NPL197] PCT/US2012/034330, International Preliminary Report on Patentability, dated Oct. 29, 2013.
[NPL205] Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.
[NPL217] U.S. Appl. No. 13/757,722, filed Feb. 1, 2013.
[NPL218] U.S. Appl. No. 13/757,794, filed Feb. 2, 2012.
[NPL219] U.S. Appl. 13/791,755, filed Mar. 8, 2013.
[NPL21] U.S. Appl. No. 13/424,479.
[NPL220] U.S. Appl. No. 13/757,792, filed Feb. 2, 2013.
[NPL222] U.S. Appl. No. 13/757,794, filed Feb. 2, 2013.
[NPL227] U.S. Appl. No. 13/837,287, filed Mar. 15, 2013.
[NPL22] U.S. Appl. No. 13/424,429.
[NPL230] Redfield, et. al, Restoration of renal response to atria! natriuretic factor in experimental low-output heat failure, Am. J. Physiol., 1989, R917-923:257.
[NPL231] Rogoza, et. al., Validation of A&D UA-767 device for the self-measurement of blood pressure, Blood Pressure Monitoring, 2000, 227-231, 5(4).
[NPL751] Office Action in European Application No. 15193720.8 dated Apr. 25, 2017.
[NPL752] International Preliminary Report on Patentability for PCT2015/060090 dated Jun. 13, 2017.
[NPL753] European Search Report for European Application EP 15193830.5 dated May 4, 2016.
[NPL754] Office Action for European Application No. 15193645.7 dated Apr. 21, 2017.
[NPL81] U.S. Appl. No. 61/480,539.
[NPL84] U.S. Appl. No. 61/480,535.
[NPL90] Nedelkov, et. al., Design of buffer exchange surfaces and sensor chips for biosensor chip mass spectrometry, Proteomics, 2002, 441-446, 2(4).
PCT/US2017/025868 International Search Report dated Jun. 29, 2017.
PCT/US2017/025868 Written Opinion dated Jun. 29, 2017.
PCTUS2017025858 International Search Report dated Jun. 29, 2017.
PCTUS2017025858 Written Opinion dated Jun. 29, 2017.

(56) References Cited

OTHER PUBLICATIONS

PCTUS2017025876 International Search Report dated Jun. 29, 2017.
PCTUS2017025876 Written Opinion dated Jun. 29, 2017.

* cited by examiner

SENSING AND STORAGE SYSTEM FOR FLUID BALANCE

CROSS-REFERENCE TO RELATED APPLICATIONS

This application is a divisional of U.S. patent application Ser. No. 14/566,674 filed Dec. 10, 2014, and the disclosure of the above-identified application is hereby incorporated by reference in its entirety.

FIELD OF THE INVENTION

The invention relates to a system for sensing and storing fluids during dialysis. The system allows for balancing fluid levels during therapy.

BACKGROUND

Kidney dialysis is a medical procedure that is performed to aid or replace some of the kidney functions in severe renal failure. Hemodialysis, hemofiltration, hemodiafiltration, and peritoneal dialysis are all replacement therapies for patients who have lost most or all of their kidney function. Dialysis can remove many of the toxins and wastes that the natural kidney would remove in healthy patients. In addition, these therapies are used to balance the electrolyte or blood salt levels and to remove excess fluid that accumulates in patients with renal failure.

In addition to removing toxins and wastes from patients with kidney disease, excess fluid accumulated in patients suffering from renal failure is generally removed by the ultrafiltration action of a dialysis procedure. Removing fluid too slowly from a patient renders the fluid removal therapy inefficient, and may force the patient to undergo a longer procedure than necessary to remove the correct amount of fluid. If the treatment is ended with insufficient fluid removal, the patient can suffer from cardiovascular and pulmonary complications related to the resultant hypervolemia. Removing too much fluid from a patient, or removing fluid too quickly from a patient, can cause a dangerous loss of blood pressure.

Some methods for controlling the amount of fluid removed from a patient are known in the art. U.S. Ser. No. 13/864,913 describes a system using two tubes connected to a pump, wherein one tube delivers fresh dialysate into the system and removes fluid from a control bag into a drain, and the second tube removes fluid into a control bag. The change in weight in the control bag is therefore due to the net ultrafiltrate removed from the patient.

U.S. Pat. No. 8,202,241B2 teaches a blood purification system comprising multiple scales. A scale is provided for each storage container in the system. The net amount of fluid removed from a patient is therefore the sum of all of the changes in weight from each of the scales. The pump rates of the pumps attached to each of the storage containers can be changed if the net rate of fluid removed from the patient varies from some pre-set rate.

US20120085707A1 teaches a blood removal system with two pumps; one on either side of a dialyzer, and a dialysate reservoir on a scale. The two pumps are in communication with a control system. The output pump drives fluid from the dialyzer into a dialysate reservoir, while the input pump drives fluid from the dialysate reservoir to the dialyzer. The net amount of fluid removed from the patient is proportional to the change in the weight of the dialysate reservoir. If the change in the weight of the dialysate reservoir does not match the fluid removal prescription, then the pump rate of the output pump can be increased, or the pump rate of the input pump can be decreased.

The known dialysis systems outlined above balance fluid levels during therapy through gravimetric control, determining the net amount of fluid added or removed to the dialysate by the changes in the weights of various containers. These additional scales or control systems add to the size, weight and cost of the dialysis system. Other known methods for fluid balancing involve the use of coordination of the pumps that add fluid to the system and the pumps that remove fluid from the system. This requires highly accurate pumping means for each pump. These additional control systems necessarily add to the size, weight and cost of the dialysis system, and the highly accurate pumps add to the total cost of the dialysis system.

Some known systems control fluid movement across the dialysis membrane by means of balance chambers that coordinately pump equal volumes of fluid into and out of the dialysate ports of the dialyzer. The balance chambers comprise a fixed volume partitioned by a membrane or piston and, as fluid enters on one side of the partition, the partition is displaced by the incoming fluid and an equal amount of fluid is expelled on the other side of the partition. In balance chamber systems, net fluid removal from the patient across the dialysis membrane is accomplished by adding a fluid removal pump in fluid communication with the dialyzer outflow port and the outflow side of the of the balance chamber partition. In such systems operation of the fluid removal pump causes a greater amount of fluid to pass out of the dialyzer than into the dialyzer, resulting in net fluid removal from the patient across the dialysis membrane. In balance chamber systems the accuracy of patient fluid removal is dependent upon the accuracy of the fluid removal pump and other factors that can degrade the volumetric accuracy of the balance chambers such as fluid leaks within the balance chamber system and gas bubbles in the dialysate. Balance chambers can result in a pulsatile flow and if a smooth flow is desired, multiple sets of balance chambers are employed to reduce the pulsatility. Balance chambers can also increase the size and weight of a hemodialysis system as well as the total fluid volume required to operate the dialysate circuit and can be undesirable for hemodialysis systems that are small, portable and operate with a reduced amount of water.

Hence, there is a need for a system that can sense and balance the fluid levels during renal therapy. There is a need for a system that can selectively and accurately control the amount of fluid added to or removed from the patient during dialysis to ensure effective treatment and patient safety, without additional equipment that can add to the size and cost of the therapy system.

SUMMARY OF THE INVENTION

The first aspect of the invention is drawn to a storage and sensing system for fluid balance during dialysis. In any embodiment of the first aspect of the invention, the storage and sensing system can comprise a control pump in a dialysate flow loop in fluid communication with a dialyzer, wherein the dialysis flow loop has a controlled volume; a fluid removal line fluidly connected to the dialysate flow loop and in communication with the control pump; an extracorporeal flow loop in fluid communication with the dialysate flow loop across a semi-permeable membrane in the dialyzer; an inflow sensor in the dialysate flow loop positioned in the dialysate flow loop at a position before the dialyzer; and an outflow sensor in the dialysate flow loop and positioned in the dialysate flow loop at a position after the dialyzer; the outflow sensor and the inflow sensor can be in electronic communication with the control pump.

In any embodiment of the first aspect of the invention, the sensing and storage system can be part of a controlled compliant dialysis system. In any embodiment of the first aspect of the invention, the dialysate flow loop is controlled compliant.

In any embodiment of the first aspect of the invention, the sensing and storage system can comprise at least one fluid pump other than the control pump fluidly connected to a fluid source and in fluid communication with the dialysate flow loop; wherein the at least one fluid pump other than the control pump is positioned in the dialysate flow loop at a position after the outflow sensor and before the inflow sensor.

In any embodiment of the first aspect of the invention, the extracorporeal flow loop can have at least one blood pump.

In any embodiment of the first aspect of the invention, the sensing and storage system can comprise more than one pump other than the control pump.

In any embodiment of the first aspect of the invention, the at least one fluid pump other than the control pump can be selected from the group comprising a sodium chloride pump in fluid communication with a sodium chloride reservoir, a water pump in fluid communication with a water reservoir, a cation infusate pump in fluid communication with a cation infusate reservoir, a bicarbonate pump in fluid communication with a bicarbonate reservoir, and combinations thereof.

In any embodiment of the first aspect of the invention, a fluid removal prescription can be set for a patient, and the pump rate of the control pump can be automatically adjusted to remove a prescribed amount of fluid based on the inputs from the inflow sensor and the outflow sensor, wherein the adjustment of the pump rate of the control pump is determined by a deviation of the fluid removal prescription from a difference between the flow rate of dialysate at the inflow sensor and the flow rate of the dialysate at the outflow sensor.

In any embodiment of the first aspect of the invention, the control pump can be a peristaltic pump. In any embodiment of the first aspect of the invention, the control pump can be capable of moving fluid bi-directionally.

In any embodiment of the first aspect of the invention, a control reservoir can be fluidly connected to the fluid removal line.

In any embodiment of the first aspect of the invention, the fluid removal line can be in fluid communication with a plumbing drain or waste line.

In any embodiment of the first aspect of the invention, the control reservoir can have a fluid capacity of between 1 L and 30 L, between 1L and 3L, between 3 L and 10 L, between 8 L and 15 L, between 12 L and 20 L, between 15 and 18 L, or between 18 L and 30.

In any embodiment of the first aspect of the invention, the control reservoir can be fluidly connected to a drain, and the system can comprise a clamp on the control reservoir to control the movement of fluid from the control reservoir to the drain.

In any embodiment of the first aspect of the invention, one or more additional flow sensors can be provided between any fluid pump and the dialyzer inlet. In any embodiment of the first aspect of the invention, one or more additional flow sensors can be provided between the dialyzer outlet and the at least one pump other than the control pump.

Any of the features described as being part of the first aspect of the invention can be included in the first aspect of the invention alone or in combination.

The second aspect of the invention is drawn to a method of controlling fluid removed from a patient during dialysis. In any embodiment of the second aspect of the invention, the method can comprise obtaining a fluid removal prescription for a patient, determining the rate of fluid flow in a dialysate flow loop on an inlet side of a dialyzer, wherein the dialysate flow loop has a controlled volume, determining the rate of fluid flow in the dialysate flow loop on an outlet side of the dialyzer, determining the deviation of the fluid removal prescription from the difference in the flow rate on the inlet side of the dialyzer and the flow rate on the outlet side of the dialyzer, and adjusting the pump rate of a control pump based on the deviation wherein the control pump is capable of moving fluid from a dialysate flow loop into a fluid removal line.

In any embodiment of the second aspect of the invention, the fluid removal line can be fluidly connected to a control reservoir. In any embodiment of the second aspect of the invention, the control reservoir can be replaced with a drain line in fluid communication with a control pump.

In any embodiment of the second aspect of the invention, one or more additional inflow sensors and/or one or more additional outflow sensors can be provided as part of an independent protective system to protect against failures in the primary control system for patient net fluid removal.

In any embodiment of the second aspect of the invention, the method can comprise removing or adding fluid to the dialysate flow path from any one or more of a control reservoir, a water reservoir, a sodium chloride reservoir, an infusate reservoir, or a bicarbonate reservoir; wherein the fluid is removed or added at a position located in the dialysate flow path located before the inflow sensor and after the outflow sensor.

In any embodiment of the second aspect of the invention, the system can further comprise a control system and the control system can automatically adjust the pump rate of the control pump based on the deviation, wherein the control pump is capable of moving fluid from the dialysate flow loop into the fluid removal line.

In any embodiment of the second aspect of the invention, the method can further comprise transferring fluid from the dialysate flow path to an extracorporeal circuit to deliver a fluid bolus to a patient.

In any embodiment of the second aspect of the invention, the method can further comprise transferring a volume of fluid from the dialysate flow path to an extracorporeal flow path, wherein transferring the volume of fluid to the extracorporeal flow path results in blood in the extracorporeal flow path being returned to a patient.

In any embodiment of the second aspect of the invention, the rate of fluid flow in the dialysate flow loop on the inlet side of the dialyzer can be determined with an inflow sensor, and the rate of fluid flow in the dialysate flow loop on the outlet side of the dialyzer can be determined with an outflow sensor.

In any embodiment of the second aspect of the invention, the fluid can be added to the dialysate flow path from the control reservoir, the water reservoir, the sodium chloride reservoir, the infusate reservoir, or the bicarbonate reservoir with the use of one or more fluid pumps.

In any embodiment of the second aspect of the invention, the method can comprise stopping the one or more fluid pumps, determining the rate of flow in the dialysate flow loop on the inlet side of the dialyzer with an inflow sensor, determining the rate of flow in the dialysate flow loop on the outlet side of the dialyzer with an outflow sensor, comparing the rate of flow on the inlet side of the dialyzer to the rate of flow on the outlet side of the dialyzer; and determining whether difference between the rate of flow is within a predetermined limit.

Any of the features described as being part of the second aspect of the invention can be included in the second aspect of the invention, either alone or in combination.

DETAILED DESCRIPTION OF THE INVENTION

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

The term "before," as used when referring to relative positions of components of a dialysis system, refers to an upstream position in the normal operational flow direction of the dialysis system. The term "after" refers to a downstream position in the normal operational flow direction of the dialysis system.

The term "bicarbonate reservoir" refers to a container that can be a stand-alone container or alternatively can be integrally formed with an apparatus for hemodialysis, hemodiafiltration, or hemofiltration. The bicarbonate reservoir can store a source of buffering material, such as sodium bicarbonate, and can be configured to interface with at least one other functional module found in systems for hemodialysis, hemodiafiltration, or hemofiltration. For example, the bicarbonate reservoir can contain at least one fluid pathway and include components such as conduits, valves, filters or fluid connection ports. The bicarbonate reservoir can be disposable or be consumable wherein the reservoir is recharged upon depletion. Specifically, the term "bicarbonate consumables container" refers to an object or apparatus having or holding a material in solid and/or solution form that is a source of bicarbonate, such as sodium bicarbonate, that is depleted during operation of the system. The object or apparatus may be single use, or may be replenished and used multiple times, for example, by refilling the object to replace the consumed material.

The term "blood pump" refers to a device to move or convey fluid through an extracorporeal circuit. The pump may be of any type suitable for pumping blood, including those known to persons of skill in the art, for example peristaltic pumps, tubing pumps, diaphragm pumps, centrifugal pumps, and shuttle pumps.

A "bolus" or "fluid bolus" is a volume of fluid. The bolus or fluid bolus can optionally be delivered to the blood of the patient.

"Bypass line" refers to a line, connected to the main line, through which fluid or gas may alternatively flow.

The term "cartridge" refers to any container designed to contain a powder, fluid, or gas made for ready connection to a device or mechanism. The container can have one or more compartments. Instead of compartments, the container can also be comprised of a system of two or more modules connected together to form the cartridge wherein the two or more modules once formed can be connected to a device or mechanism.

The term "cation infusate reservoir" refers to a source from which cations can be obtained. Examples of cations include, but are not limited to, calcium, magnesium and potassium. The source can be a solution containing cations or a dry composition that is hydrated by the system. The cation infusate reservoir is not limited to cations and may optionally include other substances to be infused into a dialysate or replacement fluid; non-limiting examples can include glucose, dextrose, acetic acid and citric acid.

The terms "communicate" and "communication" include, but are not limited to, the connection of system electrical elements, either directly or remotely, for data transmission among and between said elements. The terms also include, but are not limited to, the connection of system fluid elements enabling fluid interface among and between said elements.

The term "comprising" includes, but is not limited to, whatever follows the word "comprising." Thus, use of the term indicates that the listed elements are required or mandatory but that other elements are optional and may or may not be present.

The term "connectable" refers to being able to be joined together for purposes including, but not limited to, maintaining a position, allowing a flow of fluid, performing a measurement, transmitting power, and transmitting electrical signals. The term "connectable" can refer to being able to be joined together temporarily or permanently.

A "connector" and "for connection" as used herein describe the concept of forming a fluid connection between two components wherein fluid or gas can flow from one component, through a connector or a component for connection, to another component. The connector provides for a fluid connection in its broadest sense and can include any type of tubing, fluid or gas passageway, or conduit between any one or more components of the invention.

The term "consisting of" includes and is limited to whatever follows the phrase "consisting of" Thus, the phrase indicates that the limited elements are required or mandatory and that no other elements may be present. The term "consisting essentially of" includes whatever follows the term "consisting essentially of" and additional elements, structures, acts or features that do not affect the basic operation of the apparatus, structure or method described.

The term "container" as used herein in the context of a controlled volume circuit or flow path is a receptacle that may be flexible or inflexible for holding any fluid or solid, such as for example a spent dialysate fluid, or a sodium chloride or sodium bicarbonate solution or solid, or the like.

The terms "controlled compliance" and "controlled compliant" describe the ability to actively control the transfer of fluid volume into or out of a compartment, flow path or circuit. In any embodiment, the variable volume of fluid in a dialysate circuit or controlled compliant flow path expands and contracts via the control of one or more pumps in conjunction with one or more reservoirs. The volume of fluid in the system is generally constant (unless additional fluids are added to a reservoir from outside of the system) once the system is in operation if patient fluid volume(s), flow paths, and reservoirs are considered part of the total volume of the system (each individual volume may sometimes be referred to as a fluid compartment). The attached reservoirs allow the system to adjust the patient fluid volume by withdrawing fluid and storing the desired amount in an attached control reservoir and/or by providing purified and/or rebalanced fluids to the patient and optionally removing waste products. The terms "controlled compliance" and "controlled compliant" are not to be confused with the term "non-compliant volume," which simply refers to a vessel, conduit, container, flow path, conditioning flow path or cartridge that resists the introduction of a volume of fluid after air has been removed from a defined space such as a vessel, conduit, container, flow path, conditioning flow path or cartridge. In any embodiment, the controlled compliant system can move fluids bi-directionally. In certain cases, the bi-directional fluid movement can be across a semi-permeable membrane either inside or outside a dialyzer. The bi-directional fluid flow can also occur across, through, or between vessels, conduits, containers, flow paths, conditioning flow paths or cartridges of the invention in selected modes of operation. The term "moving fluid bi-directionally" as used in connection with a barrier, such as a semipermeable membrane, refers to the ability to move fluid across the barrier in either direction. "Moving fluid bi-directionally" also can apply to the ability to move fluid in both directions in the flow path or between a flow path and reservoir in a controlled compliant system.

The terms "controlled compliant flow path," "controlled compliant dialysate flow path" and "controlled compliant solution flow path" refer to flow paths operating within a controlled compliant system having the characteristic of controlled compliance, or of being controlled compliant as defined herein.

The term "controlled volume" refers to a flow path or system wherein a volume of fluid in the flow path or system, exclusive of any volume of fluid contained in an external reservoir, supply line, or fluid removal line, is substantially fixed. In any embodiment, a controlled volume flow path is not fluidly connected to, nor includes, an open reservoir or a reservoir having a variable volume, such as a reservoir made of a flexible material.

A "control pump" is a means capable of moving fluid through a system at a specific rate. The term "control pump" can include for example an "ultrafiltrate pump," which is a pump that is operable to pump fluid bi-directionally to actively control the transfer of fluid volume into or out of a compartment or circuit.

A "control reservoir" is a container capable of containing fluid that has been removed from a dialysate flow path or fluid to be added to a dialysate flow path.

A "control system" consists of combinations of components that act together to maintain a system to a desired set of performance specifications. The control system can use processors, memory and computer components configured to interoperate to maintain the desired performance specifications. The control system can also include fluid or gas control components, and solute control components as known within the art to maintain the performance specifications.

To "deliver a fluid bolus to a patient" means to control a dialysis system so that a volume of fluid can be delivered to a patient. Optionally, the volume of fluid can be transferred across a membrane via a dialyzer and into an extracorporeal flow path for delivery to the patient.

The term "deviation of the fluid removal prescription" refers to any difference between a fluid removal rate or volume set in a fluid removal prescription from the actual rate or volume of fluid removed during a dialysis session.

"Dialysate" is the fluid that passes through the dialyzer on the side of the dialysis membrane that is opposite to the fluid (e.g. blood) that is being dialyzed.

The term "dialysate flow loop," "dialysate flow path" or "dialysate conduit flow path" refers to any portion of a fluid pathway that conveys a dialysate and is configured to form at least part of a fluid circuit for hemodialysis, hemofiltration, hemodiafiltration or ultrafiltration.

"Dialysis" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed. The dialysate can also provide enrichment to the other fluid.

The terms "dialysis membrane," "hemodialysis membrane," "hemofiltration membrane," "hemodiafiltration membrane" and "ultrafiltration membrane" can generally be referred to as a "membrane," or can refer to a semipermeable barrier selective to allow diffusion and/or convection of solutes between blood and dialysate, or blood and filtrate, of a specific range of molecular weights in either direction through the barrier that separates blood and dialysate, or blood and filtrate, while allowing diffusive and/or convective transfer between the blood on one side of the membrane and the dialysate or filtrate circuit on the other side of the membrane.

The term "dialyzer" refers to a cartridge or container with two flow paths separated by semi-permeable membranes. One flow path is for blood and one flow path is for dialysate. The membranes can be in the form of hollow fibers, flat sheets, or spiral wound or other conventional forms known to those of skill in the art. Membranes can be selected from the following materials of polysulfone, polyethersulfone, poly(methyl methacrylate), modified cellulose, or other materials known to those skilled in the art.

The term "dialyzer inlet" refers to a fluid pathway in a dialyzer configured to allow fluid to enter the dialyzer through a fluid pathway.

The term "dialyzer outlet" refers to a fluid pathway in a dialyzer configured to allow fluid to exit the dialyzer through a fluid pathway.

A "drain" is any external fluid line designed to transport fluid that has been removed from the system and is not to be returned to the system.

"Electronic communication" refers to the connection between the electrical elements of the system, either directly or wirelessly.

The term "extracorporeal," as used herein generally means situated or occurring outside the body.

The term "extracorporeal circuit" or "extracorporeal flow loop" refers to a fluid pathway incorporating one or more components such as but not limited to conduits, valves, pumps, fluid connection ports or sensing devices configured therein such that the pathway conveys blood from a subject to an apparatus for hemodialysis, hemofiltration, hemodiafiltration or ultrafiltration and back to the subject.

"Flow" refers to the movement of a fluid or gas.

The term "flow loop" refers to a grouping of components that may guide the movement of a fluid, convey the fluid, exchange energy with the fluid, modify the composition of the fluid, measure a characteristic of the fluid and/or detect the fluid. A flow loop comprises a route or a collection of routes for a fluid to move within. Within a flow loop there may be more than one route that a volume of fluid can follow to move from one position to another position. A fluid volume may move through a flow loop such that the fluid volume recirculates, or passes the same position more than once as the fluid volume moves through a flow loop. A flow loop may operate to cause fluid volume ingress to and fluid volume egress from the flow loop. The term "flow loop" and "flow path" often may be used interchangeably.

A "fluid" is a subset of the phases of matter and can include liquids, gases, plasmas and, to some extent, plastic solids. Notably, a liquid, as used herein, can therefore also have a mixture of gas and liquid phases of matter.

The term "fluid balance" refers a fluid state in which the amount of fluid leaving a compartment (e.g. the body during dialysis) is equal to the fluid entering the compartment. In general, "fluid balance" can also refer to the maintenance of the overall balance of fluid added to a compartment and the fluid withdrawn from the compartment.

The term "fluid communication" refers to the ability of fluid or gas to move from one component or compartment to another within a system or the state of being connected, such that fluid or gas can move by pressure differences from one portion that is connected to another portion.

The terms "fluidly connectable" and "fluid connection" refer to the ability of providing for the passage of fluid or gas from one point to another point. The two points can be within or between any one or more of compartments, modules, systems, components, and rechargers, all of any type.

A "fluid pump," as used herein, refers to a pump capable of moving a fluid through a flow path.

A "fluid removal line" is a fluid pathway or fluid line for removing fluid, gas, or mixtures thereof from a fluid pathway or a fluid line during any one of hemodialysis, hemofiltration, hemodiafiltration, ultrafiltration, or peritoneal dialysis. The fluid removal line can also optionally be used to remove fluid during a cleaning or priming cycle as required. The "fluid removal line" can also introduce fluid back into a fluid pathway from which the "fluid removal line" generally operates to remove fluid depending on a required operation or desired function A "fluid removal prescription" refers to the net amount of fluid that is intended to be removed from a patient during a dialysis session.

"Infusate" is a solution of one or more salts for the adjustment of the composition of a dialysate.

An "inflow sensor" is a sensor that can measure the rate of flow of a fluid at a position at or before the inlet of the dialyzer.

An "inlet side of a dialyzer" refers to the side of a dialyzer comprising a fluid inlet.

An "operational line" or "line" is a passageway, conduit or connector that directs fluid or gas in a path used while the system is in operation.

An "outflow sensor" is a sensor that can measure the rate of flow of a fluid at a position at or after the outlet of the dialyzer.

An "outlet side of a dialyzer" refers to the side of a dialyzer comprising a fluid outlet.

The terms "pathway," "conveyance pathway," "fluid flow path," and "flow path" refer to the route through which a fluid or gas, such as dialysate or blood, travels.

A "patient" or "subject" is a member of any animal species, preferably a mammalian species, optionally a human. The subject can be an apparently healthy individual, an individual suffering from a disease, or an individual being treated for a disease.

The term "peristaltic pump" refers to a pump that operates by compression of a flexible conduit or tube through which the fluid to be pumped passes.

The term "physiologically compatible fluid" or "physiologically compatible solution" refers to a fluid that can be safely introduced into the bloodstream of a living subject.

A "predetermined limit" refers to one or more variables that are set to a defined number or range of numbers in advance.

The term "pump" refers to any device that causes the movement of fluids or gases by the application of suction or pressure.

The terms "pump rate" and "volumetric pumping rate" refer to the volume of fluid that a pump conveys per unit of time.

A "sensor" is a component capable of determining the states of one or more variables in a system.

The terms "sodium chloride reservoir" and "sodium chloride container" refer to an object that can be a stand-alone enclosure or alternatively can be integrally formed with an apparatus for hemodialysis, hemodiafiltration, or hemofiltration. The object can store a source of sodium, such as sodium chloride in solid and/or solution form, and can be configured to interface with at least one other functional module found in systems for hemodialysis, hemodiafiltration, or hemofiltration. For example, the sodium chloride reservoir or container can contain at least one fluid pathway and include components such as conduits, valves, filters or fluid connection ports.

"Sorbent cartridge" refers to a cartridge that can contain one or more sorbent materials. The cartridge can be connected to a dialysis flow path. The sorbent materials in the sorbent cartridge are used for removing specific solutes from solution, such as urea. The sorbent cartridge can have a single compartmental design wherein all sorbent materials necessary for performing dialysis are contained within the single compartment. Alternatively, the sorbent cartridge can have a modular design wherein the sorbent materials are dispersed across at least two different modules, which can be connected to form a unitary body. Once the at least two modules are connected together, the connected modules can be referred to as a sorbent cartridge, which can be fitted to a device or mechanism. When a single module contains all the sorbent materials necessary for performing dialysis, the single module can be referred to as a sorbent cartridge.

"Spent dialysate" is a dialysate contacted with blood through a dialysis membrane and contains one or more impurity, or waste species, or waste substance, such as urea.

The term "substantially inflexible volume" refers to a three-dimensional space within a vessel or container that can accommodate a maximum amount of non-compressible fluid and resists the addition of any volume of fluid above the maximum amount. The presence of a volume of fluid less than the maximum amount will fail to completely fill the vessel or container. Once a substantially inflexible volume has been filled with a fluid, removal of fluid from that volume will create a negative pressure that resists fluid removal unless fluid is added and removed simultaneously at substantially equal rates. Those skilled in the art will recognize that a minimal amount of expansion or contraction of the vessel or container can occur in a substantially inflexible volume; however, addition or subtraction of a significant volume of fluid over the maximum or minimum will be resisted.

The term "ultrafiltrate" refers to fluid that is removed from a subject by convection through a permeable membrane during hemodialysis, hemofiltration, hemodiafiltration, or peritoneal dialysis. The term "ultrafiltrate," as used herein, can also refer to the fluid in a reservoir that collects fluid volume removed from the patient, but such a reservoir may also include fluids or collections of fluids that do not originate from the subject.

An "ultrafiltrate reservoir" is a container for storing fluid removed from a subject during hemodialysis, hemofiltration, hemodiafiltration or peritoneal dialysis.

The term "ultrafiltration" refers to subjecting a fluid to filtration, where the filtered material is very small; typically, the fluid comprises colloidal, dissolved solutes or very fine solid materials, and the filter is a microporous, nanoporous, or semi-permeable medium. A typical medium is a membrane. During ultrafiltration, a "filtrate" or "ultrafiltrate" that passes through the filter medium is separated from a feed fluid. In certain instances, the use of the term "filtrate" can refer to the fluid generated during hemofiltration. In general, when transport across a membrane is predominantly diffusive as a result of a concentration driving force, the process is described herein as dialysis. When transport is primarily convective as a result of bulk flow across the membrane induced by a pressure driving force, the process is ultrafiltration or hemofiltration depending on the need for substitution solution as the membrane passes small solutes but rejects macromolecules. The term "ultrafiltration" can also refer to the fluid removal from blood during a dialysis or a hemofiltration process. That is, ultrafiltration refers to the process of passing fluid through a selective membrane, such as a dialysis or hemofiltration membrane, in dialysis, hemodiafiltration, or a filtration process.

A "valve" is a device capable of directing the flow of fluid or gas by opening, closing or obstructing one or more pathways to allow the fluid or gas to travel in a particular path. One or more valves configured to accomplish a desired flow can be configured into a "valve assembly."

The term "water reservoir" refers to an object that can be a stand-alone enclosure or alternatively can be integrally formed with an apparatus for hemodialysis, hemodiafiltration, or hemofiltration. The object can store a source of water, and can be configured to interface with at least one other functional module found in systems for hemodialysis, hemodiafiltration, or hemofiltration. For example, the water reservoir can contain at least one fluid pathway and include components such as conduits, valves, filters or fluid connection ports.

Sensing and Storage System

Figure 1:
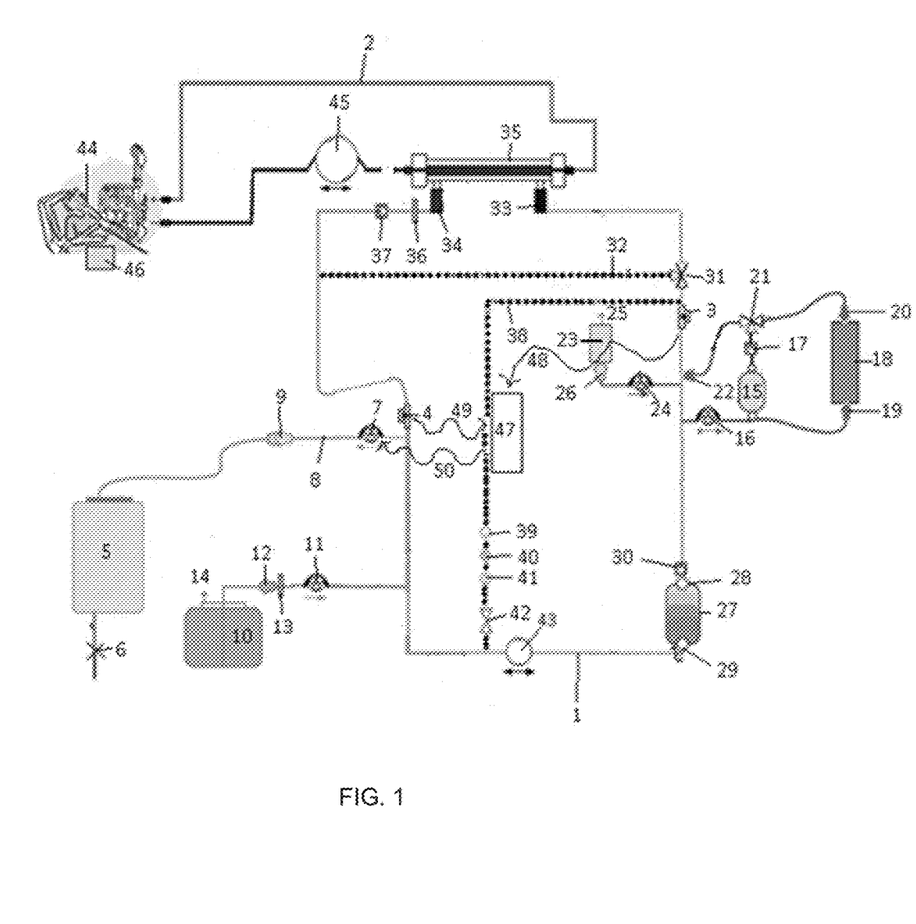
FIG. 1 shows a schematic of a dialysis system utilizing the sensing and storage system of the present invention.

The sensing system of the first and second aspects of the invention utilizes at least two flow sensors; inflow sensor 3 and outflow sensor 4, control pump 7, and a dialysate flow path 1 having a controlled volume, as defined herein, as shown in FIG. 1. The inflow sensor 3 and outflow sensor 4 can detect flow of dialysate on either side of a dialyzer 35. Inflow sensor 3 can be positioned in the dialysate flow path 1 after an optional infusate reservoir 23, sodium chloride reservoir 15, or bicarbonate reservoir 18, and therefore fluid can neither be added nor removed from the dialysate loop 1 by any fluid pumps between inflow sensor 3 and outflow sensor 4, with the exception of fluid that passes to or from the patient through a semi-permeable dialysis membrane (not shown) of the dialyzer 35. The difference between the rates of fluid flow at inflow sensor 3 and outflow sensor 4 is therefore only due to net fluid changes due to movement of fluid from the extracorporeal circuit 2 to the dialysate loop 1 and from the dialysate loop 1 into a control reservoir 5. In any embodiment of the first and second aspects of the invention, the control reservoir 5 can be an ultrafiltrate reservoir, configured to receive fluid removed by ultrafiltration.

Because net fluid flow between the extracorporeal circuit 2 and dialysate loop 1 having a controlled volume of the dialysis system can be precisely determined by the difference in the rates of flow between inflow sensor 3 and outflow sensor 4, accurate control over fluid balance to the patient can be achieved using only control pump 7, without the use of balance chambers, scales or gravimetric control, and without coordination of the actions of fluid pumps, such as infusate pump 24, water pump 11, and sodium chloride pump 16. The pump rate of the control pump 7 only needs to be adjusted based on the deviation of the prescribed fluid removal session for a patient from the difference between the rates of dialysate flow at inflow sensor 3 and at outflow sensor 4. In general, adjusting the pump rate of a control pump 7 based on a deviation generally refers to the process of changing the pump rate of the control pump 7 in order to make the fluid removal rate closer to the fluid removal rate set in a fluid removal prescription.

A control system 47 may automatically adjust the pump rate of control pump 7 by sending signal 50 to control pump 7, based on the difference between the dialysate flow rate measured by the inflow sensor 3, sent to the control system 47 by signal 48, and dialysate flow rate measured by the outflow sensor 4, sent to the control system 47 by signal 49, as compared to the prescribed rate for a particular patient 44. Regardless of the volume of fluid added from bicarbonate reservoir 18, sodium chloride reservoir 15 or infusate reservoir 23, the pump rate of the control pump 7 can be adjusted to maintain the proper net fluid flow from the patient 44 to the control reservoir 5. The signals between the pumps, flow sensors and the control system 47 may be sent wirelessly or through wired communication.

Fluid removed from the patient during dialysis by ultrafiltration can flow through fluid removal line 8 and control reservoir connector 9 and into the control reservoir 5. In any embodiment of the first and second aspects of the invention, the control reservoir 5 may be large enough to accommodate all of the fluid that needs to be removed during dialysis. In any embodiment of the first and second aspects of the invention, the control reservoir 5 can be smaller, and drain clamp 6 can be opened when the control reservoir 5 is filled to allow draining from the control reservoir 5 into a drain. In any embodiment of the first and second aspects of the invention, connector 9 being in fluid communication with control reservoir 5 is not required. Instead, fluid removal line 8 can directly connect to a drain (not shown). In other embodiments, the fluid removal line 8 can serve as a conduit to introduce fluid rather than remove fluid back into a fluid pathway or fluid line as required. For example, the fluid removal line 8 can serve to facilitate movement of fluid during a blood rinse back operation or cleaning cycle away from a control reservoir 5 and back into the dialysate flow path 1 where a suitable fluid can be provided. For example, a cleaned dialysate fluid blood, or any other suitable fluid can be retuned back to a patient as a fluid bolus at an end of a treatment via the fluid removal line 8 During treatment, fluid may be added from sodium chloride reservoir 15 in order to control the sodium chloride concentration of the dialysate; from bicarbonate reservoir 18 in order to control the bicarbonate concentration of the dialysate; and from cation infusate reservoir 23 in order to control the concentration of other cations in the dialysate, such as calcium, potassium or magnesium. The control reservoir 5, therefore, can be large enough to hold the sum of these volumes. In any embodiment of the first and second aspects of the invention, the control reservoir 5 can have a fluid capacity of about 15 L, which is generally enough to contain all necessary fluids for a normal dialysis session. In any embodiment of the first and second aspects of the invention, the control reservoir 5 may be larger or smaller. In any embodiment of the first or second aspects of the invention, the control reservoir 5 can be between any of 1 L-30 L, 1-3 L, 1-5 L, 3-10 L, 8-15 L, 12-20 L, 15-18 L or 18-30 L. Clamp 6 can control drainage from the control reservoir 5. In any embodiment of the first and second aspects of the invention where the control reservoir 5 is not large enough to hold all of the necessary volume, the control reservoir 5 can be fluidly connected to a drain (not shown) and clamp 6 can be opened during treatment to drain the control reservoir 5 and allow for additional fluid removal.

The pumps utilized by the fluid balancing system of the first and second aspects of the invention can be any type known in the art, including but not limited to, gear pumps, peristaltic pumps, diaphragm pumps, and impeller pumps. Because the patient fluid removal rate can be precisely controlled by the control pump 7 utilizing the inflow sensor 3 and outflow sensor 4, the fluid pumps used to add water, sodium chloride, infusates and bicarbonate need not be absolutely precise. If more fluid than is necessary is added by any one of these pumps, the control system 47 can automatically detect a change in the difference between flow measured at inflow sensor 3 and outflow sensor 4 and adjust the pump rate of control pump 7 automatically.

In any embodiment of the first and second aspects of the invention, control pump 7 may be operated bi-directionally. That is, control pump 7 may be operated in the influx direction in order to move fluid from the control reservoir 5 to the dialysate flow loop 1; or control pump 7 may be operated in the efflux direction in order to move fluid from the dialysate flow loop 1 into the control reservoir 5. When the control pump 7 is operated in the influx direction to move fluid from the control reservoir 5 to the dialysate flow loop 1, check valve 37 ensures that the fluid volume introduced to the dialysate flow path 1 from control reservoir 5 must first pass through sorbent cartridge 27 before passing into the dialyzer.

Blood is circulated from the patient 44 to the dialyzer 35 through the extracorporeal circuit 2 by blood pump 45. Blood pressure monitor 46 can be used to monitor the blood pressure of the patient 44 before, during or after treatment. The measured blood pressure can correspond to the rate of removal of fluid from the patient. If fluid is removed from the patient 44 at too high of a rate, the patient's blood pressure can drop to dangerous levels. In any embodiment of the first and second aspects of the invention, the pump rate of control pump 7 can automatically be adjusted due to changes in patient blood pressure detected by blood pressure monitor 46. If the blood pressure detected by blood pressure monitor 46 is too low, the pump rate of control pump 7 can automatically be reduced. In any embodiment of the first and second aspects of the invention, the pump rate of control pump 7 can be increased if the measured blood pressure does not show a significant drop.

The dialysis system shown in FIG. 1 is a controlled volume dialysis system. This means that net passive movement of fluid volume across the dialysis membrane (not shown) due to operational pressure changes can be eliminated. The system shown in FIG. 1 does not contain any open or flexible reservoirs, and therefore the volume of fluid recirculating through the dialysate flow path is substantially fixed. In any embodiment of the first and second aspects of the invention, the dialysis system or dialysate flow loop can be controlled compliant. In any embodiment of the first or second aspects of the invention, the user can make the system operate as a controlled compliant dialysis system by ensuring that all reservoirs or drains are closed or have a substantially inflexible volume. Because there is no net passive movement of fluid volume across the dialysis membrane, the net movement of fluid across the dialysis membrane is controlled by the operational pumps of the system. In any embodiment of the first and second aspects of the invention, removal of fluid from the dialysate flow path 1 can result in a vacuum being created in the dialysate flow path 1, due to the fact that the dialysate flow path 1 has a substantially inflexible volume. In the event of factors that tend to increase pressure on the extracorporeal side of the dialysis membrane, such as increased blood flow rate or blood viscosity, pressure across the membrane will automatically be equalized due to the limited volume of the dialysate flow path and the non-compressible nature of the dialysate. In the event of factors that tend to increase pressure on the dialysate side of the dialysis membrane, such as increased dialysate flow rate, net movement of water from the controlled volume dialysate flow path to the extracorporeal flow path is prevented by a vacuum that would form in the controlled volume flow path in the event of such a movement, due to the fixed volume of the controlled volume flow path.

Other sorbent-based regenerative hemodialysis systems known in the art have dialysate solution reservoirs that are located in the dialysate flow path between the dialyzer outlet 34 and the dialyzer inlet 33. In these known systems the dialysate reservoirs are in some cases open reservoirs and in other cases they are flexible volumes such as bags. One skilled in the art will understand that, in such systems, the inclusion of such reservoirs in between the dialyzer outlet 34 and the dialyzer inlet 33 inhibits precise control of patient net fluid volume removal by means of inflow sensor 3, outflow sensor 4, and control pump 7 because dialysate flow path 1 will no longer have the characteristic of a controlled volume dialysate flow path. Thus, the application of inflow sensor 3, outflow sensor 4 and control pump 7 to control net patient fluid volume removal within the context of a controlled volume flow path is a critical feature of the present invention.

During dialysis, blood will be circulated from the patient 44, through an extracorporeal circuit 2, to dialyzer 35, and back to the patient 44. Dialysate will be circulated in a dialysate flow path 1 on the opposite side of the dialyzer 35 from the patient's blood. Blood contacts a semi-permeable membrane (not shown) in the dialyzer 35 that separates the extracorporeal circuit 2 from the dialysate circuit 1. Waste species in the patient's blood can cross the semi-permeable membrane and enter the dialysate.

Fluid movement through the dialysate circuit 1 of the first and second aspects of the invention is controlled by dialysate pump 43. Dialysate enters the dialyzer 35 through dialyzer inlet connector 33 and leaves through dialyzer outlet connector 34. The spent dialysate can travel past outlet filter 36. Check valve 37 serves to ensure that any fluid added to the system cannot travel past dialyzer connector 34 and into the dialyzer 35, but instead must travel through the circuit and sorbent cartridge 27 to reach dialyzer 35. The control pump 7 through connector 9 and water pump 11 through connector 12 can be used to draw water out of the dialysate circuit 1, and thereby cause a net removal of fluid from the patient, or add water to the dialysate circuit 1. Fluid removed from the patient can pass through fluid removal line connector 9 and into the control reservoir 5.

Water reservoir 10 can be used to add fluid to the dialysate circuit as needed. Water reservoir pump 11 can draw water out of the water reservoir 10, through water reservoir connector 12 and past water filter 13. Vent 14 allows the pressure to be equalized as water is removed from the water reservoir 10. The spent dialysate then travels into sorbent cartridge 27 where the toxins are removed from the spent dialysate. The spent dialysate enters the sorbent cartridge 27 through sorbent cartridge inlet connector 29, and leaves through sorbent cartridge outlet connector 28. Sorbent cartridge check valve 30 ensures that fluid cannot enter the sorbent cartridge 27 in the opposite direction, or leak from the dialysate flow path when sorbent cartridge 27 is disconnected at connector 28.

Sodium chloride, bicarbonate, and other cation infusates may be added to the dialysate. Sodium chloride pump 16 can draw dialysate into the sodium chloride reservoir 15 or bicarbonate reservoir 18, through bicarbonate reservoir connectors 19 and 20. Diverter valve 21 can control the addition of sodium chloride or bicarbonate from the reservoirs into the dialysate. Sodium chloride check valve 17 ensures that fluid cannot pass through the sodium chloride reservoir 15 in the opposite direction. Fluid from the sodium chloride reservoir 15 and bicarbonate reservoir 18 can enter the dialysate flow loop through connector 22. Cation infusate pump 24 can control the addition of infusate from cation infusate reservoir 23 into the dialysate through cation infusate reservoir connector 26. Vent 25 in cation infusate source 23 can allow the equalization of pressure during addition of the infusate.

In any embodiment of the first and second aspects of the invention, a small amount of dialysate can be drawn off by chemical sensor valve 42 to detect the levels of chemicals in the dialysate before returning to the dialyzer 35. By opening sensor valve 42, fluid can be drawn through sensor line 38 and to ammonia sensor 39, pH sensor 40, and carbon dioxide sensor 41. If the levels of chemicals in the dialysate are outside of the proper concentrations, the appropriate infusates can be added to the dialysate as described above, or dialyzer bypass valve 31 can be activated to prevent the dialysate from reaching dialyzer inlet port 33. In any embodiment of the first and second aspects of the invention, chemical sensors 39, 40 and 41 can optionally be located in the main dialysate flow path and a separate sensor line 38 is not required.

The spent dialysate then passes by dialyzer bypass valve 31, which can cause the dialysate to bypass the dialyzer 35 if necessary through dialyzer bypass line 32. In normal operation, dialyzer bypass valve 31 will be set to allow dialysate through dialyzer 35. The dialysate then passes through dialyzer inlet connector 33, and back into the dialyzer 35.

Failure to precisely control patient net fluid removal can be hazardous to the patient. Inadequate fluid removal can lead to blood pressure derangements and pulmonary edema. Excessive removal can lead to lead to a dangerous drop in blood pressure. For this reason, independent protective systems that can detect a failure in the ultrafiltration control system and act to prevent patient harm due to net fluid removal errors are beneficial. The ultrafiltration control system of the dialysate flow path of the first and second aspects of the invention shown in FIG. 1 can be periodically self-tested by temporarily stopping pumps 7, 11, 24, and 16 to stop all dialysate flow path 1 fluid ingress and egress to make the ultrafiltration rate equal to zero, and then comparing the readings at inflow sensor 3 to outflow sensor 4. If the flow sensors providing measurements to the control system are operating properly, the reading at inflow sensor 3 will be identical to the reading from outflow sensor 4 within predetermined error limits. If the error between inflow sensor 3 and outflow sensor 4 is outside of predetermined limits, then the dialysis process can be stopped before the patient is harmed. Further, those of skill in the art will understand that the protective system described will not be possible with systems known in the art that have an open or flexible reservoir in the main dialysate flow path 1 between the dialyzer outlet 34 and dialyzer inlet 33.

In any embodiment of the first and second aspects of the invention, redundant flow sensors can be added as part of an independent protective system. For example, one or more additional redundant outflow sensors can be placed between the dialyzer 35 and the first fluid pump after the dialyzer 35. The additional outflow sensor can be used to determine whether the primary outflow sensor 4 is properly functioning. If the additional, redundant outflow sensor detects a flow that is different from outflow sensor 4, the difference may show that outflow sensor 4 is not working properly. In response, dialysis can be stopped until a determination of which sensors are not working properly can be made. Similarly, one or more redundant inflow sensors can be included between the dialyzer 35 and the first fluid pump in the flow loop prior to the dialyzer 35. As with the redundant outflow sensors, redundant inflow sensors can provide an independent protective system by ensuring that inflow sensor 3 is properly functioning.

The flow path of the first and second aspects of the invention described in FIG. 1 can also control patient net fluid volume when a bolus of fluid is delivered from the dialysate flow path 1 to the extracorporeal circuit 2 and to the patient 44. To deliver a precise bolus of fluid to the patient, the pumping rate of control pump 7 in the efflux direction can be reduced, stopped or, in any embodiment of the first and second aspects of the invention, reversed to provide influx flow to dialysate flow path 1. If the incoming fluid volume provided by the other metering pumps, such as cation infusate pump 24 and water infusion pump 11 is not sufficient to provide the desired patient fluid bolus, the rate of one or more of the pumps, such as water infusion pump 11 can be increased to provide a precisely controlled fluid bolus volume to the patient at the desired rate. If the addition of water by means of pump 11 causes the concentrations of sodium or bicarbonate to become less than desired, pump 16 can be operated to infuse sodium chloride and/or sodium bicarbonate to achieve the desired concentrations. This functionality beneficially allows the a fluid bolus to be provided to the patient without requiring the expense of a bag of saline or the time required to connect the saline bag to the flow path. The reduced time required to initiate delivery of the fluid bolus to the patient is especially beneficial when rapid intervention is required to correct a severe hypotensive episode in the patient. In general, transferring a volume of fluid from a dialysate flow path to an extracorporeal flow path will be understood to refer to a process of adding fluid to a dialysate flow path such that fluid is transferred across a dialyzer into an extracorporeal flow path. One skilled in the art will understand that the described functionalities are not possible with known systems having open or flexible reservoirs in the flow path, nor with other known systems, for example systems with volumetric balance chambers.

The blood in the extracorporeal circuit 2 is normally returned to the patient 44 at the end of a hemodialysis treatment. Commonly, the fluid used to return the blood from the extracorporeal circuit 2 is provided by means of a saline bag connected to a port on the extracorporeal circuit 2. One skilled in the art will understand that the fluid bolus volume control function described herein can also be employed to provide physiologically compatible fluid to the extracorporeal circuit 2 to assist in returning the blood at the end of a hemodialysis treatment. This functionality beneficially allows the blood to be returned to the patient 44 without requiring the expense of a bag of saline or the time required to connect the saline bag to the flow path. One skilled in the art will understand that this functionality is not possible with known systems having open or flexible reservoirs in the flow path, nor with other known systems, for example systems with volumetric balance chambers.

Figure 2:
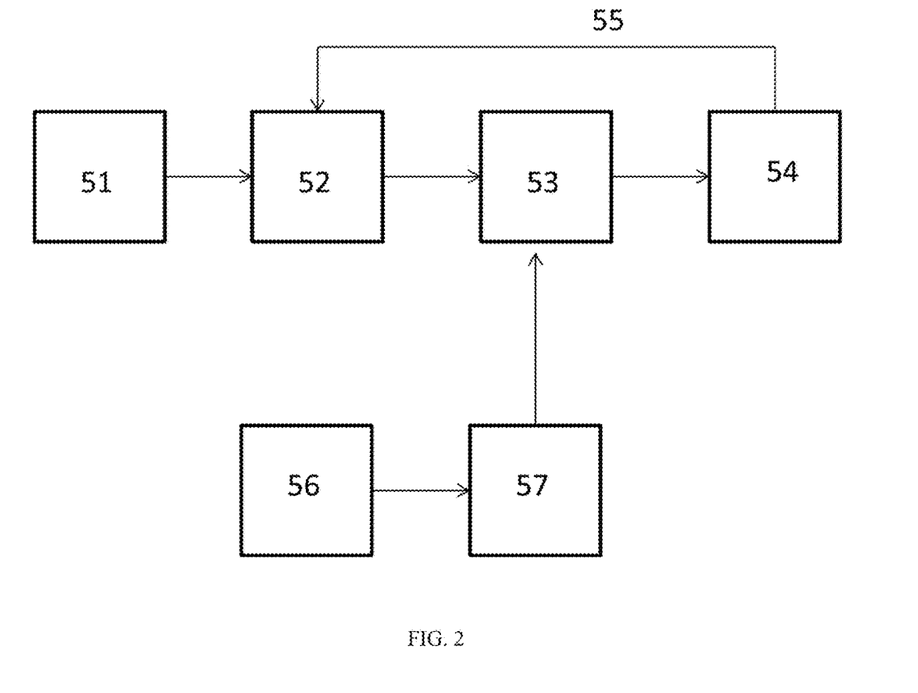
FIG. 2 is a flow diagram showing the operation of the fluid sensing and storage system.

FIG. 2 is a flow diagram showing the operation of the system of the first and second aspects of the invention. Initially, a fluid removal prescription will be set for the patient 51. This is the amount of fluid that needs to be removed from the patient and the rate at which fluid will be removed from the patient. The pump rate of the control pump will be set to remove the necessary amount of fluid at the set rate 52. A control system can monitor the flow rates of the dialysate at the inflow sensor and the outflow sensor 53. The difference in the flow rates at the inflow sensor and outflow sensor is only due to the net fluid movement from the dialysate flow loop to the blood flow loop and the removal of fluid to by the control pump. If the rate of fluid movement from the extracorporeal flow loop to the dialysate flow loop is not equal to the fluid removal prescription, the pump rate of the control pump can be altered, as shown by arrow 55. During the treatment, data can be sent to the control system concerning the blood pressure of the patient and the concentrations of chemicals in the dialysate 56. If necessary, fluid can be added from a sodium chloride reservoir, sodium bicarbonate reservoir, fluid reservoir or water reservoir to the dialysate flow loop 57, as explained above. The addition of fluid to the dialysate flow loop can affect the net movement of fluid from the extracorporeal flow loop to the dialysate flow loop. This effect can be determined by monitoring the difference in flow rates at the inflow sensor and outflow sensor 53, and so the addition of fluid to the dialysate flow loop does not affect the calculation of the net movement of fluid from the dialysate flow loop to the blood flow loop 54.

The inflow sensor and outflow sensor of the present invention can be any type of flow sensor known in the art that can detect the flow of a fluid at a specific point. One non-limiting example of a flow sensor is the commercially available 8000 Series Liquid Flow Meter from Proteus Industries, Inc. In any embodiment of the first and second aspects of the invention, the flow sensor can be a turbine type flow sensor having an optical encoder to allow the flow rate to be measured. However, any commercially available or non-commercially available sensor that can accurately measure the flow of a fluid is contemplated by this invention.

One skilled in the art will understand that various combinations and/or modifications and variations can be made in the dialysis system depending upon the specific needs for operation. Moreover features illustrated or described as being part of an aspect of the invention can be included in the aspect of the invention, either alone or in combination.

We claim:

1. A sensing and storage system for fluid balance during dialysis, comprising;

a control pump in a dialysate flow loop in fluid communication with a dialyzer, wherein the dialysate flow loop has a controlled volume;

a fluid removal line fluidly connected to the dialysate flow loop and in communication with the control pump;

an extracorporeal flow loop in fluid communication with the dialysate flow loop across a semi-permeable membrane in the dialyzer;

an inflow sensor in the dialysate flow loop and positioned in the dialysate flow loop at a position before the dialyzer;

an outflow sensor in the dialysate flow loop and positioned in the dialysate flow loop at a position after the dialyzer;

a sensor line having a first end positioned in the dialysate flow loop after the inflow sensor and before the dialyzer and a second end positioned after the outflow sensor wherein the sensor line has one or more additional sensors positioned on the sensor line; and a control system configured to receive data from the inflow sensor and the outflow sensor; wherein said control system is configured to electronically communicate with the control pump, wherein the control system is configured to utilize a fluid balancing system configured to automatically adjust a pump rate of the control pump based on a difference between the flow measured at inflow sensor and outflow sensor to maintain a controlled volume in the dialysate flow loop.

2. The sensing and storage system of claim 1, wherein the dialysate flow loop is a controlled compliant dialysate flow loop.

3. The sensing and storage system of claim 1, further comprising at least one fluid pump other than the control pump fluidly connected to a fluid source and in fluid communication with the dialysate flow loop; wherein the at least one fluid pump other than the control pump is positioned in the dialysate flow loop at a position after the outflow sensor and before the inflow sensor.

4. The sensing and storage system of claim 3, wherein the at least one fluid pump other than the control pump is selected from the group consisting of a sodium chloride pump in fluid communication with a sodium chloride reservoir, a water pump in fluid communication with a water reservoir, a cation infusate pump in fluid communication with a cation infusate reservoir, a bicarbonate pump in fluid communication with a bicarbonate reservoir, and combinations thereof.

5. The sensing and storage system of claim 3, wherein the control system is in electronic communication with the at least one fluid pump other than the control pump.

6. The sensing and storage system of claim 1, wherein the control system is configured to maintain a controlled volume in the dialysate flow loop based on a fluid removal prescription for a patient.

7. The sensing and storage system of claim 3, wherein one or more additional flow sensors are provided between the at least one fluid pump and a dialyzer inlet.

8. The sensing and storage system of claim 3, further comprising one or more additional flow sensors positioned between a dialyzer outlet and the at least one fluid pump other than the control pump.

9. The sensing and storage system of claim 1, wherein the control system is configured to periodically self-test by adjusting a pump rate of one or more pumps to make an ultrafiltration flow rate equal to zero and comparing a first reading at an inflow sensor to a second reading at an outflow sensor, wherein if said first reading and second reading are identical within a predetermined error limit, then the control system is operating properly.

10. The sensing and storage system of claim 1, wherein the control system is configured to determine a deviation of a fluid removal prescription from a difference in a flow rate measured by the inflow sensor and a flow rate measured by the outflow sensor.

11. The sensing and storage system of claim 10, wherein the control system is configured to automatically adjust the pump rate of the control pump to lower the deviation of the fluid removal prescription from the difference in the flow rate measured by the inflow sensor and the flow rate measured by the outflow sensor.

12. The sensing and storage system of claim 3, wherein all of the pumps are configured to periodically stop for the inflow sensor and the outflow sensor to measure a first flow rate and a second flow rate, respectively.

13. The sensing and storage system of claim 12, wherein the control system is configured to stop dialysis in response to the first flow rate being not identical to the second flow rate within a predetermined error limit.

14. The sensing and storage system of claim 1, wherein the control system is configured to obtain the controlled volume in the dialysate flow loop from a fluid removal prescription for a patient.

15. The sensing and storage system of claim 1, wherein the control system is in electronic communication with a water pump; and wherein the control system is configured to automatically adjust a pump rate of the water pump based on the difference between the flow measured at inflow sensor and outflow sensor to maintain the controlled volume in the dialysate flow loop.

16. The sensing and storage system of claim 1, wherein the control system is configured to deliver a fluid bolus to a patient by increasing a pump rate of a water pump.

17. The sensing and storage system of claim 1, the control system in electronic communication with a sensor measuring patient blood pressure; the control system configured to adjust the pump rate of the control pump in response to changes in patient blood pressure.

18. The sensing and storage system of claim 1, wherein the dialysate flow loop comprises a sorbent cartridge.

19. The sensing and storage system of claim 1, wherein the control pump is capable of moving fluid bi-directionally and wherein the system is configured to control patient net fluid volume by reversing the control pump from an efflux direction to an influx direction.

20. The sensing and storage system of claim 19, further comprising a control reservoir fluidly connected to the fluid removal line.

21. The sensing and storage system of claim 1, wherein the one or more of additional sensors positioned on the sensor line are one or more of ammonia sensor, pH sensor, and carbon dioxide sensor.

* * * * *